(12) United States Patent
Kallioniemi et al.

(10) Patent No.: US 9,260,758 B2
(45) Date of Patent: Feb. 16, 2016

(54) CELLULAR ARRAYS AND METHODS OF DETECTING AND USING GENETIC DISORDER MARKERS

(75) Inventors: Olli-P Kallioniemi, Rockville, MD (US); Uwe Richard Muller, Painted Post, NY (US); Guido Sauter, Basel (SE); Juha Kononen, Rockville, MD (US); Maarit Barlund, Tampere (FI)

(73) Assignees: The United States of America as Represented by the Secretary of the Department of Health and Human Services, Washington, DC (US); Abbott Molecular Inc., Des Plaines, IL (US)

( * ) Notice: Subject to any disclaimer, the term of this patent is extended or adjusted under 35 U.S.C. 154(b) by 0 days.

(21) Appl. No.: 12/284,188

(22) Filed: Sep. 19, 2008

(65) Prior Publication Data

US 2009/0092993 A1    Apr. 9, 2009

Related U.S. Application Data

(63) Continuation of application No. 11/151,679, filed on Jun. 13, 2005, now abandoned, which is a continuation of application No. 09/971,742, filed on Oct. 4, 2001, now Pat. No. 6,905,823, which is a continuation of application No. 09/429,448, filed on Oct. 28, 1999, now abandoned.

(60) Provisional application No. 60/106,038, filed on Oct. 28, 1998, provisional application No. 60/150,493, filed on Aug. 24, 1999.

(51) Int. Cl.
| | |
|---|---|
| C12Q 1/68 | (2006.01) |
| B01L 3/00 | (2006.01) |
| G01N 1/28 | (2006.01) |
| G01N 1/31 | (2006.01) |
| G01N 33/50 | (2006.01) |
| G01N 33/543 | (2006.01) |
| G02B 21/34 | (2006.01) |
| G01N 1/08 | (2006.01) |
| G01N 1/36 | (2006.01) |

(52) U.S. Cl.
CPC ............. *C12Q 1/6886* (2013.01); *B01L 3/5085* (2013.01); *C12Q 1/6809* (2013.01); *C12Q 1/6837* (2013.01); *C12Q 1/6841* (2013.01); *G01N 1/2813* (2013.01); *G01N 1/312* (2013.01); *G01N 33/5005* (2013.01); *G01N 33/54306* (2013.01); *G02B 21/34* (2013.01); *B01J 2219/00659* (2013.01); *B01J 2219/00702* (2013.01); *B01J 2219/00743* (2013.01); *C12Q 2600/106* (2013.01); *C12Q 2600/112* (2013.01); *C12Q 2600/118* (2013.01); *G01N 1/08* (2013.01); *G01N 2001/282* (2013.01); *G01N 2001/288* (2013.01); *G01N 2001/368* (2013.01)

(58) Field of Classification Search
CPC ................. C12Q 2537/157; C12Q 2539/103; C12Q 2543/10; C12Q 1/6809; C12Q 1/6837; C12Q 1/6841; C12Q 2565/501; C12Q 1/6886; C12Q 2600/106; C12Q 2600/112; C12Q 2600/118

See application file for complete search history.

(56) References Cited

U.S. PATENT DOCUMENTS

| | | |
|---|---|---|
| 4,914,022 A | 4/1990 | Furmanski et al. |
| 5,002,377 A | 3/1991 | Battifora et al. |
| 5,591,574 A | 1/1997 | Orth et al. |
| 5,665,549 A | 9/1997 | Pinkel et al. |
| 5,690,894 A | 11/1997 | Pinkel et al. |
| 5,693,610 A | 12/1997 | Matsunaga et al. |
| 5,800,992 A | 9/1998 | Fodor et al. |
| 5,821,218 A | 10/1998 | Toback et al. |
| 5,843,767 A | 12/1998 | Beattie |
| 5,856,097 A | 1/1999 | Pinkel |
| 5,976,790 A | 11/1999 | Pinkel et al. |
| 6,001,621 A | 12/1999 | Godowski et al. |
| 6,156,522 A | 12/2000 | Keay |

(Continued)

OTHER PUBLICATIONS

Adnane, J et al. BEK and FLG two receptors to members of the FGF family, are amplifed in subsets of human breast cancers. 1991 Oncogene vol. 6 pp. 659-663.*

(Continued)

*Primary Examiner* — James Martinell
(74) *Attorney, Agent, or Firm* — Pierce Atwood LLP; Kevin M. Farrell; David J. Wilson

(57) ABSTRACT

A method is disclosed for rapid molecular profiling of tissue or other cellular specimens by placing a donor specimen in an assigned location in a recipient array, providing copies of the array, and performing a different biological analysis of each copy. The results of the different biological analyses are compared to determine if there are correlations between the results of the different biological analyses at each assigned location. In some embodiments, the specimens may be tissue specimens from different tumors, which are subjected to multiple parallel molecular (including genetic and immunological) analyses. The results of the parallel analyses are then used to detect common molecular characteristics of the genetic disorder type, which can subsequently be used in the diagnosis or treatment of the disease. The biological characteristics of the tissue can be correlated with clinical or other information, to detect characteristics associated with the tissue, such as susceptibility or resistance to particular types of drug treatment. Other examples of suitable tissues which can be placed in the matrix include tissue from transgenic or model organisms, or cellular suspensions (such as cytological preparations or specimens of liquid malignancies or cell lines).

6 Claims, 11 Drawing Sheets

(56) References Cited

U.S. PATENT DOCUMENTS 6,210,878 B1 4/2001 Pinkel et al.
6,333,153 B1 12/2001 Fishel

OTHER PUBLICATIONS

Tannheimer, Stacey et al. Characterization of fibroblast growth factor receptor 2 over expression in the human breast cancer cell line SUM-52PE. 2000 Breast Cancer Research vol. 2 pp. 311-320.*
Sasaki, Teruo et al. Detection of gene amplification and deletion in high grade gliomas using a genome DNA microarray (GenoSensor Array 300). 2003. Brain Tumor Pathology. vol. 20 pp. 59-63.*
Kallioniemi, Anne et al. Detection and mapping of amplified DNA sequences in breast cancer by comparative genomic hybridization. 1994. PNAS vol. 91 pp. 2156-2160.*
Kallioniemi, Anne et al. Gene copy number analysis by fluorescence in situ hybridization and comparative genomic hybridization. 1996. Methods: A Companion to Methods in Enzymology. vol. 9 pp. 113-121.*
Houldsworth, Jane et al. Comparative genomic hybridization: an overview. 1994. American Journal of Pathology. vol. 145 No. 6 pp. 1253-1260.*
Visscher, Daniel et al. Evaluation of MYC and Chromosome 8 Copy Number in Breast Carcinoma by Interphase Cytogenetics. Genes, Chromosomes, & Cancer Jan. 1997 vol. 18 pp. 1-7.*
Gene Card for FGFR2 http://www.genecards.org/cgi-bin/carddisp.pl?gene=FGFR2&search=fgfr2 accessed online Dec. 28, 2010.*
Gene Card for FGFR1 http://www.genecards.org/cgi-bin/carddisp.pl?gene=FGFR1&search=fgfr1 accessed online Dec. 28, 2010.*
The Gene Card for PDGFB online at http://www.genecards.org/cgi-bin/carddisp.pl?gene=PDGFB&search=pdgfb accessed Nov. 16, 2011.*
Saint-Ruf et al. Genes Chromosomes & Cancer 1990 vol. 2 pp. 18-26.*
Forozan et al. TIG Oct. 1997 vol. 13 No. 10 pp. 405-409.*
Forozon et al., "Genome Screening by Comparative Genomic Hybridization", Trends in Genetics, 13(10): 405-409, (Oct. 1997).
M. Heiskanen et al., "High-resolution CGH array analysis reveals unexpected gene amplifications in breast cancer" The American Journal of Human Genetics, 63(4) 1998, Abstract.
Joos et al., "mapping of Chromosomal . . . Genomic Hybridization", Genes Chromosomes and Cancer, 14:267-276 (1995).
Kononen et al., "Tissue Microarrays for high-throughput molecular profiling of tumor specimens," Nature Medicine, 4(7):844-847 (Jul. 1998).
Leveen et al., "Negative trans-acting Mechanisms controlling Expression of Platelet-derived Growth Factor A and B mRNA in Somatic cel Hybrids," Experimental Cell Research, 207: 283-289, (1989).
Pinkel et al., "High Resolution Analysis of DNA . . . to Microarrays", Nature Genetics, 20:207-211, (1998).
P.Schraml et al., "Tumor tissue arrays for gene amplification detection in multiple different tumor types" The American Journal of Human Genetics, 63(4) 1998, Abstract No. 845.
Bubendorf, L. et al., Tissue-microarray technology ("tissue chip") for molecular profiling of Prostate cancer progression: Making FISH a high-throughput tool for cancer genetics, The American journal of Human Genetics, 63(4), Supplement to vol. 63, Oct. 1998, Session 20: Plenary Session, p. A2, paragraph 1.
Schraml, P.H., et al., Tumor tissue arrays for gene amplification detection in multiple different tumor types. The American journal of Human Genetics, 63(4), Supplement to vol. 63, Oct. 1998, Posters: Cytogenetics, p. A149, paragraph 845.
Tsujimoto, et al., article, "Amplification of growth factor receptor genes and DNA ploidy pattern in the progression of gastric cancer", Springer-Verlag, Jun. 3, 1997, pp. 383-389 (7 pages).
Drugan, et al., article, "Fibroblast growth factor receptor expression reflects cellular differentiation in human oral squamous carcinoma cell lines", Carcinogenesis vol. 19, No. 6, 1998, pp. 1153-1156 (5 pages).
Luqmani et al.; "Expression of FGFR2 BEK and K-SAM mRNA Variants in Normal and Malignant Human Breast"; European Journal of Cancer; 32A(3):518-524 (1996).
Burns, et al. "Non-isotopic detection of in situ nucleic acid in cervix: an updated protocol" Journal Clinical Pathology; 1988; vol. 41; pp. 897-899.
Ross, et al. "Prognostic significance of HER-2/neu gene amplification status by fluorescence in situ hybridization of prostate carcinoma" American Cancer Society; Jun. 1, 1997; vol. 79, No. 11; pp. 2162-2170.
Leitzel, et al. "Elevated Plasma Platelet-derived growth factor B-chain levels in cancer patients" Cancer Research; Aug. 15, 1991; vol. 51; pp. 4149-4154.
Houldsworth, et al. "Comparative genomic hybridization: an overview" American Journal of Pathology; Dec. 1994; vol. 145; No. 6; pp. 1253-1260.
Velculescu, et al. "Serial analysis of gene expression" Science; Oct. 20, 1995; vol. 270; pp. 484-487.
Scheck, et al. ."BCNU-Resistant human glioma cells with over-representation of chromosomes 7 and 22 demonstrate increased copy number and expression of platelet-derived growth factor genes" Genes, Chromosomes & Cancer; 1993; vol. 8; pp. 137-148.
Kallioniemi, et al. "Comparative genomic hybridiztion for molecular cytogenetic analysis of solid tumors" Science; Oct. 30, 1992; vol. 258; pp. 818-821.
SCHENA "Genome analysis with gene expression microarrays" BioEssays; 1996; vol. 18; No. 5; pp. 427-431.

\* cited by examiner

SPECIMEN

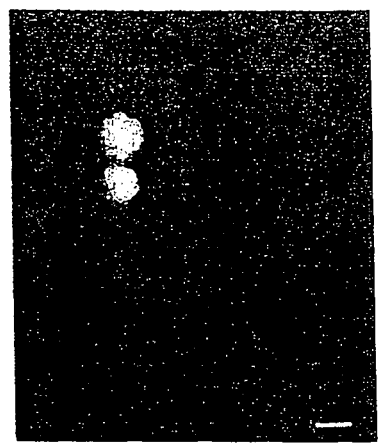
Figure 10B
Figure 10C
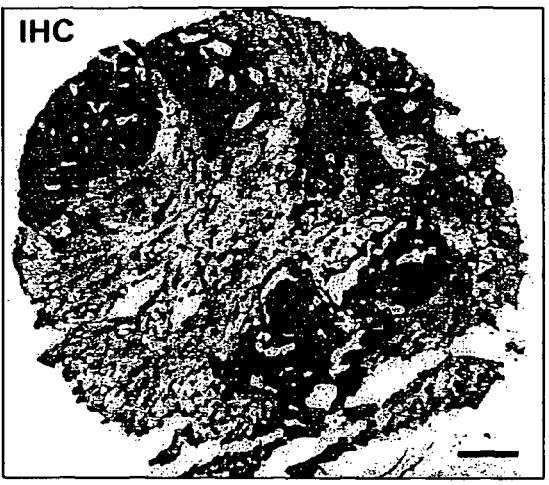
Figure 10D
Figure 10E

CELLULAR ARRAYS AND METHODS OF DETECTING AND USING GENETIC DISORDER MARKERS

CROSS-REFERENCE TO RELATED APPLICATIONS

This application claims priority from U.S. Provisional Application Ser. No. 60/106,038, filed on Oct. 28, 1998, and U.S. Provisional Application Ser. No. 60/150,493, filed on Aug. 24, 1999, both of which are incorporated herein by reference in their entirety.

FIELD OF THE INVENTION

The invention relates to the screening of tissue samples and genomic regions to discover markers for genetic disorders such as cancer.

BACKGROUND OF THE INVENTION

Biological mechanisms of many diseases have been clarified by microscopic examination of tissue specimens. Histopathological examination has also permitted the development of effective medical treatments for a variety of illnesses. In standard anatomical pathology, a diagnosis is made on the basis of cell morphology and staining characteristics. Tumor specimens, for example, can be examined to characterize the tumor type and predict the aggressiveness of the tumor. Although this microscopic examination and classification of tumors has improved medical treatment, the microscopic appearance of a tissue specimen stained by standard methods (such as hematoxylin and eosin) can often reveal only a limited amount of diagnostic or molecular information.

Recent advances in molecular medicine have provided an even greater opportunity to understand the cellular mechanisms of disease, and select appropriate treatments with the greatest likelihood of success. Some hormone dependent breast tumor cells, for example, have an increased expression of estrogen receptors on their cell surfaces, which indicates that the patient from whom the tumor was taken will likely respond to certain anti-estrogenic drug treatments. Other diagnostic and prognostic cellular changes include the presence of tumor specific cell surface antigens (as in melanoma), the production of embryonic proteins (such as α-fetoprotein in liver cancer and carcinoembryonic glycoprotein antigen produced by gastrointestinal tumors), and genetic abnormalities (such as activated oncogenes in tumors). A variety of techniques have evolved to detect the presence of these cellular abnormalities, including immunophenotyping with monoclonal antibodies, in situ hybridization with probes, and DNA amplification using the polymerase chain reaction (PCR).

The development of new molecular markers of clinical importance has been impeded by the slow and tedious process of evaluating biomarkers in large numbers of clinical specimens. For example, hundreds of tissue specimens representing different stages of tumor progression have to be evaluated before the importance of a given marker can be assessed. Since the number of antibodies, as well as probes for mRNA or DNA targets is increasing rapidly, only a small fraction of these can ever be tested in large numbers of clinical specimens.

Various methods have been explored to prepare samples of multiple tissues or nucleic acids on one slide or plate.

SUMMARY OF THE INVENTION

The invention is based on the discovery that two very different types of arrays can be used in combination in new methods to rapidly and accurately detect, with high resolution, genomic copy number alterations, such as gene amplifications or deletions, that can serve as markers for various genetic disorders such as cancers and trisomies.

Thus, the invention features methods of detecting particular genomic "target" regions (nucleic acid sequences) that correspond to specific genetic disorders, e.g., one or more different types of tumors or hereditary genetic diseases, by combining tissue microarray technology with other technologies, such as high-throughput genomics. These methods are used to identify molecular characteristics, such as structural changes in genes or proteins, and copy number or expression alterations of genes, and to correlate these results with disease prognosis or therapy outcome to identify novel targets for gene prevention, early diagnosis, disease classification, or prognosis, and to identify therapeutic agents. High-throughput technologies include cDNA arrays and Comparative Genomic Hybridization ("CGH") arrays.

The invention also includes methods of preparing new arrays of nucleic acids (genes), e.g., representative of specific types of tumors (tumor-specific diagnostic gene arrays); probes that hybridize selectively to these genomic target regions; methods of preparing the probes; methods of using the probes to screen for and/or diagnose specific genetic disorders; compositions that interact with the genomic target regions to treat the genetic disorders; and methods of treating the genetic disorders using these compositions.

In general, in one aspect the invention features a method of parallel analysis of tissue specimens, by obtaining a plurality of donor specimens; placing each donor specimen in an assigned location in a recipient array; using a genosensor comparative genomic hybridization (gCGH) array to identify a biomarker to test on the recipient array; obtaining a plurality of sections from the recipient array in a manner that each section contains a plurality of donor specimens that maintain their assigned locations; performing on each section a different biological analysis using the biomarker; and comparing the results of the different biological analyses in corresponding assigned locations of different sections to determine if there are correlations between the results of the different biological analyses at each assigned location. For example, the biomarker can be selected by high-throughput genetic analysis, and the biomarker can include a numerical alteration of a chromosome, chromosomal region, gene, gene fragment, or locus.

The results can be compared by determining if there is an alteration of a gene by examining a marker for gene alteration. For example, the alteration can be an amplification of PDGFB in breast, lung, colon, testicular, endometrial, or bladder cancer.

In another embodiment, the invention features a method of analyzing gene amplification in a tissue specimen by screening multiple genes in a tissue specimen with a genosensor comparative genomic hybridization (gCGH) array that detects which genes are amplified in the tissue specimen; and screening multiple tissue specimens in a tissue array with a nucleic acid probe to detect which genes are amplified in the tissue specimens; wherein the result of screening multiple genes is used to select the nucleic acid probe to screen the multiple tissue specimens, or wherein the result of screening multiple tissue specimens is used to select the array that detects which genes are amplified.

In this method, the gCGH array can be assayed for a gene amplification, or a genetic or molecular marker that reflects this amplification. The CGH array can be a microarray that contains target loci that undergo amplification in cancer.

The invention also features a method of analyzing a biological sample for a genetic disorder by exposing a genosensor comparative genomic hybridization (gCGH) array of genomic regions to a nucleic acid sample from a cell with a known specific genetic disorder, and identifying as a biomarker a genomic region to which the nucleic acid hybridizes; obtaining a candidate probe that hybridizes to the biomarker; exposing the candidate probe to a tissue specimen array to determine a statistical measure of hybridization of the candidate probe; selecting a candidate probe having a statistically significant measure of hybridization; and using a selected candidate probe to analyze a biological sample for the genetic disorder. This analysis of the biological sample can provide diagnostic or prognostic information.

In addition, the invention features a method of detecting the presence of cancerous cells in a specimen, by determining whether platelet derived growth factor beta (PDGFB) is amplified in the specimen, amplification indicating the presence of cancerous cells in the specimen, e.g., a lung, bladder, or endometrial tissue specimen.

In another aspect, the invention features a method for detecting a genomic target sequence that is associated with a specific genetic disorder by contacting a plurality of genomic regions in a genosensor comparative genomic hybridization (gCGH) array with a nucleic acid test sample including nucleic acid fragments that collectively represent DNA from a cell with a known specific genetic disorder under conditions that allow the nucleic acid fragments to hybridize to one or more candidate genomic regions; measuring the amount of nucleic acid test sample hybridized to the candidate genomic regions, if any, and selecting a candidate genomic region corresponding to an altered amount of hybridized test sample nucleic acid compared to a control sample of normal DNA; preparing a nucleic acid probe that hybridizes to the selected candidate genomic region; contacting a plurality of tissue samples with the probe under conditions that allow the probe to hybridize to nucleotide sequences in the tissue samples; and selecting a candidate genomic region corresponding to a probe that hybridizes co a significant number of tissue samples as a genomic target sequence that is associated with the specific genetic disorder.

As used herein, a "polypeptide" is any chain of amino acids, regardless of length or post-translational modification (e.g., glycosylation or phosphorylation).

A "gene amplification" is an increase in the copy number of a gene, as compared to the copy number in normal tissue. An example of a genomic amplification is an increase in the copy number of an oncogene. A "gene deletion" is a deletion of one or more nucleic acids normally present in a gene sequence, and in extreme examples can include deletions of entire genes or even portions of chromosomes.

A "genomic target sequence" is a sequence of nucleotides located in a particular region in the human genome that corresponds to one or more specific loci, including genetic abnormalities, such as a nucleotide polymorphism, a deletion, or an amplification.

A "genetic disorder" is any illness, disease, or abnormal physical or mental condition that is caused by an alteration in one or more genes or regulatory sequences (such as an amplification, mutation, deletion, or translocation).

"Comparative Genomic Hybridization" or CGH is a technique of differential labeling of test DNA and normal reference DNA, which are hybridized simultaneously to chromosome spreads, as described in Kallioniemi et al., Science, 258:818-821, 1992.

A "nucleic acid array" refers to an arrangement of nucleic acid (such as DNA or RNA) in assigned locations on a matrix, such as that found in cDNA or CGH arrays.

A "microarray" is an array that is miniaturized so as to require microscopic examination for visual evaluation.

A "DNA chip" is a DNA array in which multiple DNA molecules (such as cDNAs) of known DNA sequences are arrayed on a substrate, usually in a microarray, so that the DNA molecules can hybridize with nucleic acids (such as cDNA or RNA) from a specimen of interest. DNA chips are further described in Ramsay, *Nature Biotechnology*, 16:40-44, 1998.

"Gene expression microarrays" refers to microscopic arrays of cDNAs printed on a substrate, which serve as a high density hybridization target for mRNA probes, as in Schena, *BioEssays* 18:427-431, 1996.

"Serial Analysis of Gene Expression" or "SAGE" refers to the use of short sequence tags to allow the quantitative and simultaneous analysis of a large number of transcripts in tissue, as described in Velculescu et al., *Science*, 270:484-487, 1995.

"High throughput genomics" refers to application of genomic or genetic data or analysis techniques that use microarrays or other genomic technologies to rapidly identify large numbers of genes or proteins, or distinguish their structure, expression or function from normal or abnormal cells or tissues.

A "tumor" is a neoplasm that may be either malignant or non-malignant. "Tumors of the same tissue type" refers to primary tumors originating in a Particular organ (such as breast, prostate, bladder or lung). Tumors of the same tissue type may be divided into tumors of different sub-types (a classic example being bronchogenic carcinomas (lung tumors) which can be an adenocarcinoma, small cell, squamous cell, or large cell tumor).

A "cellular" specimen is one which contains whole cells, and includes tissues, which are aggregations of similarly specialized cells united in the performance of a particular function. Examples include cells from the skin, breast, prostate, blood, testis, ovary and endometrium.

A "cellular suspension" is a liquid in which cells are dispersed, and may include a uniform or non-uniform suspension. Examples of cellular suspensions are those obtained by fine-needle aspiration from tumor sites, cytology specimens (such as vaginal fluids for preparing Pap smears, washes (such as bronchial washings), urine that contains cells (for example in the detection of bladder cancer), ascitic fluid (for example obtained by abdominal paracentesis), or other body fluids.

A "cytological preparation" is a pathological specimen, such as vaginal fluids, in which a cellular suspension can be converted into a smear or other form for pathological examination or analysis.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention provides a rapid means of identifying not only specific genomic abnormalities present in a tissue, but the importance and statistical significance of these abnormalities in hundreds or thousands of tissues, to provide relevant diagnostic and prognostic information, as well as potential targets for therapeutic agents.

Other features and advantages of the invention will be apparent from the following detailed description, and from the claims.

BRIEF DESCRIPTION OF THE DRAWINGS

FIG. 10B is a magnified view of a portion of the slide in FIG. 10A, showing results of erbB2 mRNA in situ hybridization on a tissue array from the region in the small rectangle in FIG. 10A.

FIG. 10C is an electrophoresis gel showing that high molecular weight DNA and RNA can be extracted from the breast cancer specimens fixed in cold ethanol.

FIG. 10D is an enlarged view of one of the tissue samples of the array in FIG. 10A, showing an immunoperoxidase staining for the erbB2 antigen.

FIG. 10E is a view similar to FIG. 10D, showing high level erbB2 gene amplification detected by fluorescent in situ hybridization (FISH) of tissue in the array by an erbB2 DNA probe.

DETAILED DESCRIPTION

The use of tissue arrays in combination with other array techniques can provide information about the frequency of a multitude of genetic alteration or gene expression patterns (including normal gene expression patterns) in a variety of tissue types (such as different types of tumors), and in tissue of a particular histological type (such as a tumor of a specific type, such as intraductal breast cancer), as well as the tissue distribution of molecular markers tested.

In one specific embodiment of the combined DNA and tissue arrays, the DNA array may be a cDNA or genomic microarray chip that allows a plurality (hundreds, thousands, or even more) of different nucleic acid sequences to be affixed to the surface of a support to form an array. Such a chip may, for instance carry an array of cDNA clones, oligonucleotides, or large-insert genomic P1, BAC, or PAC clones. These arrays enable the analysis of hundreds of genes or genomic fragments at once to determine their expression or copy number in a test specimen.

A high-throughput DNA chip can be used together with high-throughput tissue array technology. Such hybrid inventions include using a DNA array to screen a limited number of tumor samples for expression or copy number of one or more (for example thousands of) specific genes or DNA sequences. Probes containing the gene of interest may then be used to screen a tissue microarray that contains many different tissue specimens (such as a variety of breast tumors or prostate tumors) to determine if the identified gene or genetic locus is similarly altered in these tumors. For instance, a cDNA chip can be used to screen a human breast cancer cell line, to identify one or more genes that are overexpressed or amplified in that particular breast cancer. A probe, corresponding to the identified gene, would then be used to probe a tissue array containing a plurality of tissue samples from different breast cancers, or even tumors of different types (such as lung or prostate cancer). Such a probe could be made by labeling the identical clone used in the DNA array (for example with a fluorescent or radioactive marker). The presence of the gene in related (or unrelated) tumors would be revealed by the pattern of hybridization of the probe to the tissue array.

Another embodiment includes a method of preparing a diagnostic tumor-specific gene array.

Embodiments of FIGS. 1 to 12

Figure 3:
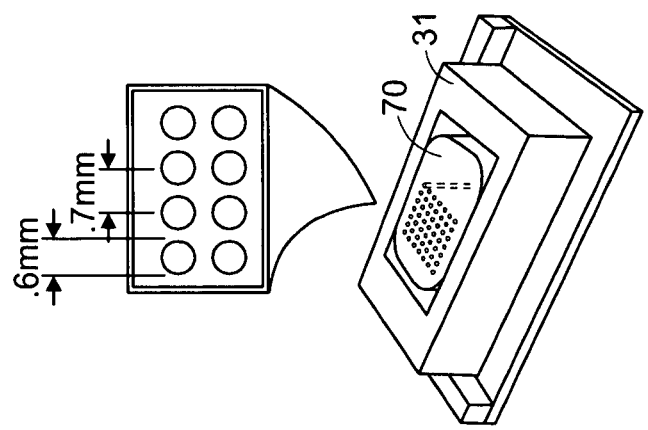
FIG. 3 is a schematic, perspective view of a recipient block into which the donor specimen has been placed.
Figure 2:
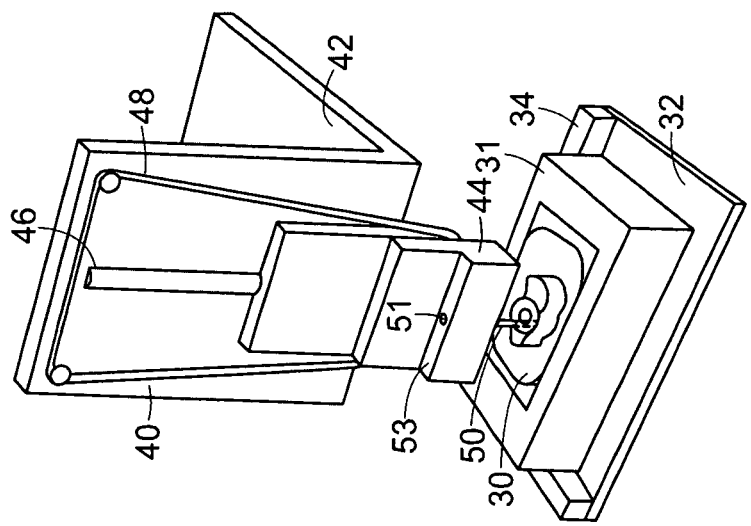
FIG. 2 is a view similar to FIG. 1, but in which the punch has been advanced to obtain a donor specimen sample.
Figure 1:
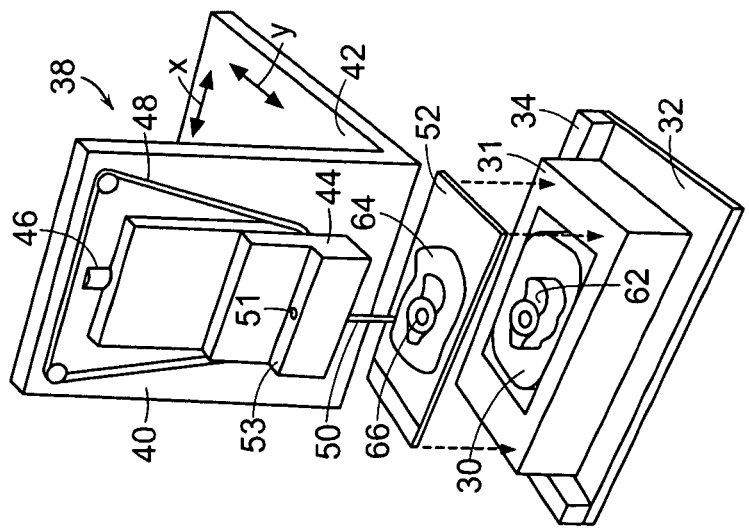
FIG. 1 is a schematic perspective view of a first embodiment of the punch device of the present invention, showing alignment of the punch above a region of interest of donor tissue in a donor block.

A first embodiment of a device for making the microarrays of the present invention is shown in FIGS. 1 and 2, in which a donor block 30 (of tissue) is shown in a rectangular container 31 mounted on a stationary platform 32 having an L-shaped edge guide 34 that maintains donor container 31 in a predetermined orientation on platform 32. A punch apparatus 38 is mounted above platform 32, and includes a vertical guide plate 40 and a horizontal positioning plate 42. The positioning plate 42 is mounted on an x-y stage (not shown) that can be precisely positioned with a pair of digital micrometers.

Vertical guide plate 40 has a flat front face that provides a precision guide surface against which a reciprocal punch base 44 can slide along a track 46 between a retracted position shown in FIG. 1 and an extended position shown in FIG. 2. An elastic band 48 helps control the movement of base 44 along this path, and the limits of advancement and retraction of base 44 are set by track member 46, which forms a stop that limits the amplitude of oscillation of base 44. A thin wall stainless steel tube punch 50 with sharpened leading edges is mounted on the flat bottom face of base 44, so that punch 50 can be advanced and retracted with respect to platform 32, and the container 31 on the platform. The hollow interior of punch 50 is continuous with a cylindrical bore through base 44, and the bore opens at opening 51 on a horizontal lip 53 of base 44.

FIG. 1 shows that a thin section of tissue, stained with hematoxylin-eosin or other stains, can be obtained from donor block 30 and mounted on a slide 52 (with appropriate preparation and staining) so that anatomic and micro-anatomic structures of interest can be located in the block 30. Slide 52 can be held above donor block 30 by an articulated arm holder 54 (FIG. 9) with a clamp 56 which securely holds an edge of a transparent support slide 58. Arm holder 54 can articulate at joint 60, to swivel between a first position in which support slide 58 is locked in position above container 31, and a second position in which support slide 58 moves horizontally out of the position shown in FIG. 9 to permit free access to punch 50.

Figure 9:
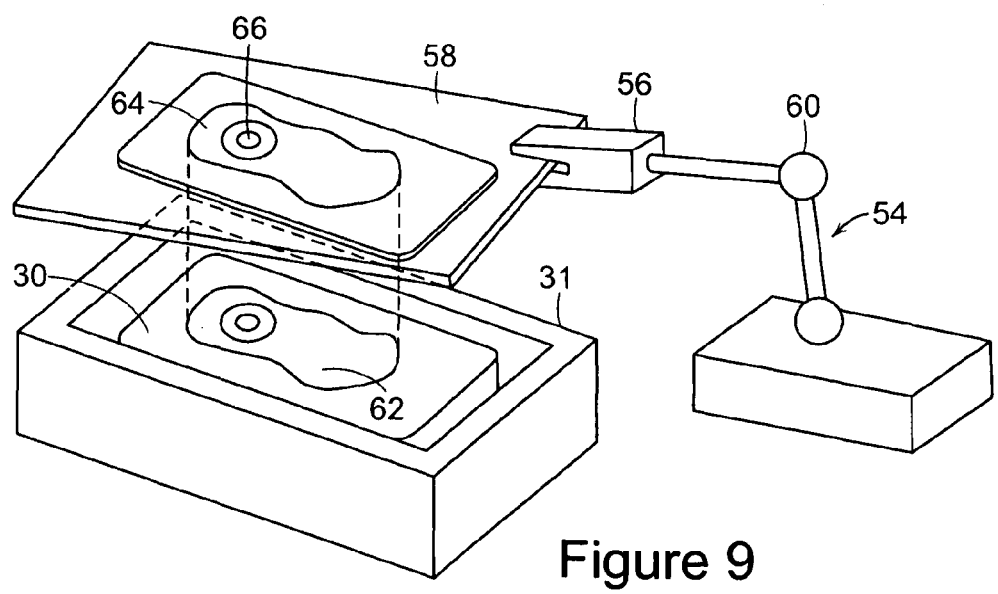
FIG. 9 is a perspective view of a locking device for holding a slide mounted specimen above the tissue in the donor block to locate a region of interest.

In operation, the rectangular container 31 is placed on platform 32 (FIG. 1) with edges of container 31 abutting edge guides 34 to hold container 31 in a selected position. A donor block 30 is prepared by embedding a gross tissue specimen (such as a three dimensional tumor specimen 62) in paraffin. A thin section of donor block 30 is shaved off, stained, and mounted on slide 52 as thin section 64, and slide 52 is then placed on support slide 58 and positioned above donor block 30 as shown in FIG. 9. Slide 52 can be moved around on support slide 58 until the edges of thin section 64 are aligned with the edges of the gross 4 pathological specimen 62, as shown by the dotted lines in FIG. 9. Arm 54 is then locked in the first position, to which the arm can subsequently return after displacement to a second position.

A micro-anatomic or histologic structure of interest 66 can then be located by examining the thin section through a microscope (not shown). If the tissue specimen is, for example, an adenocarcinoma of the breast, then the location of the structure of interest 66 may be an area of the specimen in which the cellular architecture is suggestive of specific features of the cancer, such as invasive and noninvasive components. Once the structure of interest 66 is located, the corresponding region of tissue specimen 62 from which the thin section structure of interest 66 was obtained is located immediately below the structure of interest 66. As shown in FIG. 1, positioning plate 42 can be moved in the x and y directions (under the control of the digital micrometers or a joystick), or the donor block can be moved for larger distances, to align punch 50 in position above the region of interest of the donor block 30, and the support slide 58 is then horizontally pivoted away from its position above donor block 30 around pivot joint 60 (FIG. 9).

Punch 50 is then introduced into the structure of interest in donor block 30 (FIG. 2) by advancing vertical guide plate 40 along track 46 until plate 44 reaches its stop position (which is preset by apparatus 38). As punch 50 advances, its sharp leading edge bores a cylindrical tissue specimen out of the donor block 30, and the specimen is retained within the punch as the punch reciprocates back to its retracted position shown in FIG. 1. The cylindrical tissue specimen can subsequently be dislodged from punch 50 by advancing a stylet (not shown) into opening 51. The tissue specimen is, for example, dislodged from punch 50 and introduced into a cylindrical receptacle of complementary shape and size in an array of receptacles in a recipient block 70 shown in FIG. 3.

One or more recipient blocks 70 can be prepared prior to obtaining the tissue specimen from the donor block 30. Block 70 can be prepared by placing a solid paraffin block in container 31 and using punch 50 to make cylindrical punches in block 70 in a regular pattern that produces an array of cylindrical receptacles of the type shown in FIG. 3. The regular array can be generated by positioning punch 50 at a starting point above block 70 (for example a corner of the prospective array), advancing and then retracting punch 50 to remove a cylindrical core from a specific coordinate on block 70, then dislodging the core from the punch by introducing a stylet into opening 51. The punch apparatus or the recipient block is then moved in regular increments in the x and/or y directions, to the next coordinate of the array, and the punching step is repeated. In the specific disclosed embodiment of FIG. 3, the cylindrical receptacles of the array have diameters of about 0.6 mm, with the centers of the cylinders being spaced by a distance of about 0.7 mm (so that there is a distance of about 0.05 mm between the adjacent edges of the receptacles).

In a specific example, core tissue biopsies having a diameter of 0.6 mm and a height of 3-4 mm, were taken from selected representative regions of individual "donor" paraffin-embedded tumor blocks and precisely arrayed into a new "recipient" paraffin block (20 mm×45 mm). H&E-stained sections were positioned above the donor blocks and used to guide sampling from morphologically representative sites in the tumors. Although the diameter of the biopsy punch can be varied, 0.6 mm cylinders have been found to be suitable because they are large enough to evaluate histological patterns in each element of the tumor array, yet are sufficiently small to cause only minimal damage to the original donor tissue blocks, and to isolate reasonably homogenous tissue blocks.

Up to 1000 such tissue cylinders, or more, can be placed in one 20×45 mm recipient paraffin block. Specific disclosed diameters of the cylinders are 0.1-4.0 mm, for example 0.5-2.0 mm, and most specifically less than 1 mm, for example 0.6 mm. Automation of the procedure, with computer guided placement of the specimens, allows very small specimens to be placed tightly together in the recipient array.

Figure 4:
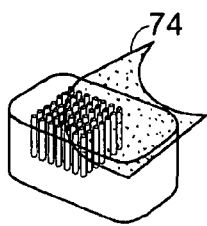
FIGS. 4-8 are schematic diagrams illustrating steps in the preparation of thin section arrays from the recipient block.
Figure 5:
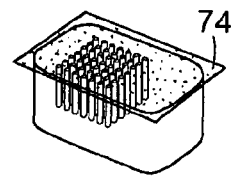
Figures 6, 7:
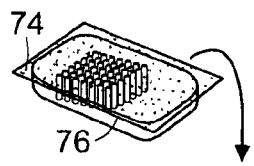
Figure 7:
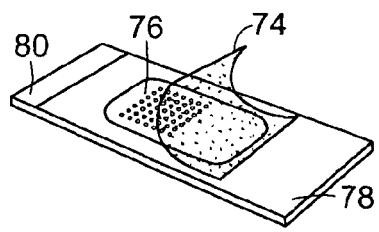
Figure 8:
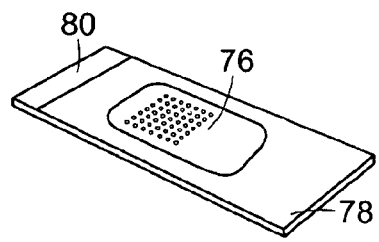

FIG. 4 shows the array in the recipient block after the receptacles of the array have been filled with tissue specimen cylinders. The top surface of the recipient block is then covered with an adhesive film 74 from an adhesive coated tape sectioning system (Instrumedics) to help maintain the tissue cylinder sections in place in the array once it is cut. The array block may be warmed at 37° C. for 15 minutes before sectioning, to promote adherence of the tissue cores and allow smoothing of the block surface when pressing a smooth, clean surface (such as a microscope slide) against the block surface.

With the adhesive film in place, a 4-8 μm section of the recipient block is cut transverse to the longitudinal axis of the tissue cylinders (FIG. 5) to produce a thin microarray section 76 (containing tissue specimen cylinder sections in the form of disks) that is transferred to a conventional specimen slide 78. The microarray section 76 is adhered to slide 78, for example by adhesive on the slide. The film 74 is then peeled away from the underlying microarray member 76 to expose it for processing. A darkened edge 80 of slide 78 is suitable for labeling or handling the slide.

Breast cancer tissue specimens were fixed in cold ethanol to help preserve high-molecular weight DNA and RNA, and 372 of the specimens were fixed in this manner. At least 200 consecutive 4-8 μm tumor array sections can be cut from each block providing targets for correlated in situ analyses of multiple molecular markers at the DNA, RNA, or protein level, including copy number or expression of multiple genes. This analysis is performed by testing for different gene molecular targets (e.g., DNA or RNA sequences or antigens defined by antibodies) in separate array sections, and comparing the results of the tests at identical coordinates of the array (which correspond to tissue specimens from the same tissue cylinder obtained from donor block). This approach enables measurement of virtually hundreds of molecular characteristics from every tumor, thereby facilitating construction of a large series of correlated genotypic or phenotypic characteristics of uncultured human tumors.

Figure 10A:
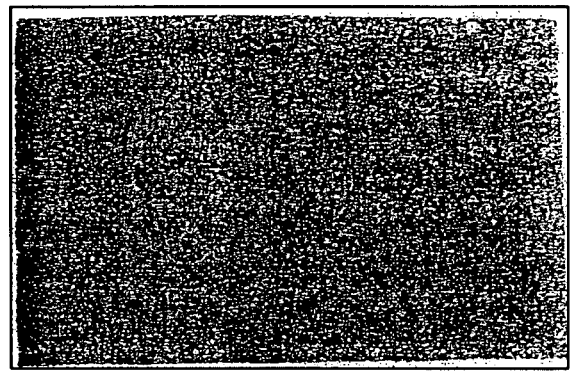
FIG. 10A is a view of an H&E stained, thin section tissue array mounted on a slide for microscopic examination.
Figure 10A:
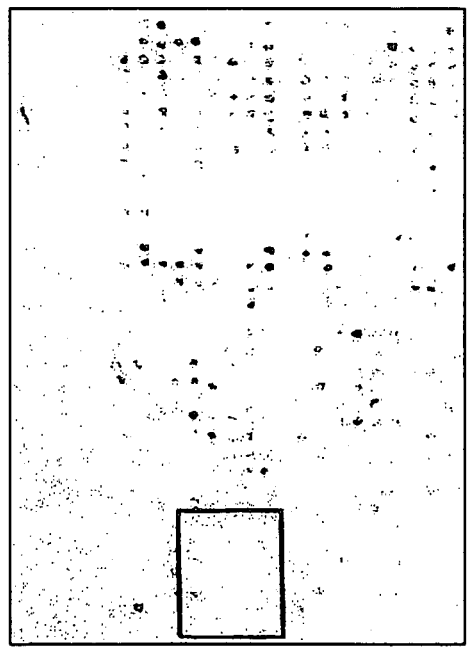

An example of a single microarray 76 containing 645 specimens is shown in FIG. 10A. An enlarged section of the microarray (highlighted by a rectangle in FIG. 10A) is shown in FIG. 10B, in which an autoradiogram of erbB2 mRNA in situ hybridization illustrates that two adjacent specimens in the array demonstrate a strong hybridization signal. FIG. 10C illustrates electrophoresis gels which demonstrate that high molecular weight DNA and RNA can be extracted from breast cancer specimens fixed in ethanol at 4 (C overnight.

One of the tissue specimens that gave the fluorescent "positive" signals was also analyzed by immunoperoxidase staining, as shown in FIG. 10D, where it was confirmed (by the dark stain) that the erbB2 gene product was present. A DNA probe for the erbB2 gene was used to perform fluorescent in situ hybridization (FISH). FIG. 10D shows one of the tumor array elements, which demonstrated high level erbB2 gene amplification. The insert in FIG. 10E shows three nuclei with numerous tightly clustered erbB2 hybridization signals and two copies of the centromeric reference probe. Additional details about these assays are given in Examples 1-4 below.

Figures 11A, 11B, 11C, 11D:
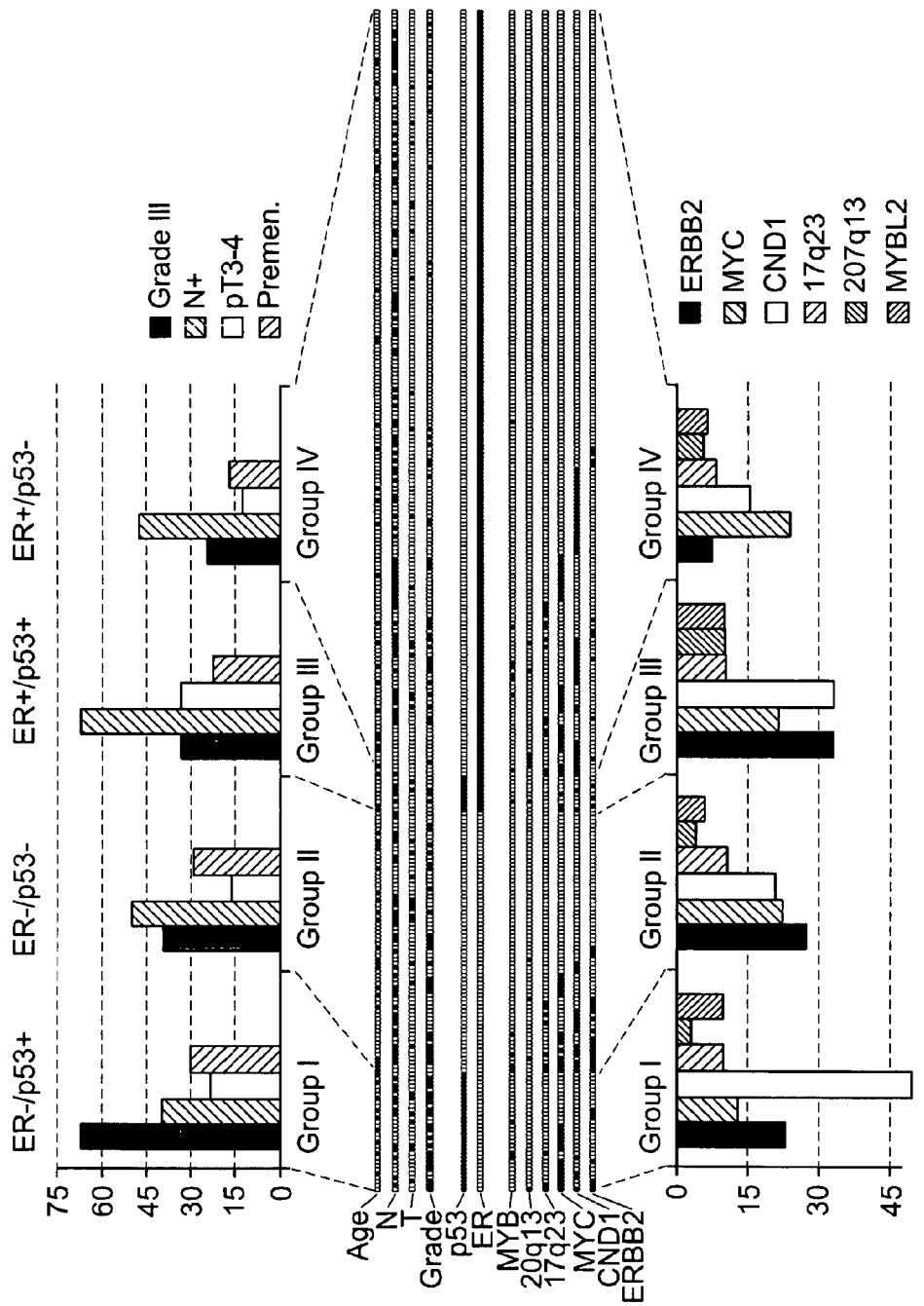
FIGS. 11A, 11B, 11C and 11D are schematic views illustrating an example of parallel analysis of arrays obtained by the method of the present invention.

The potential of the array technology of the present invention to perform rapid parallel molecular analysis of multiple tissue specimens is illustrated in FIGS. 11A-11D, where the y-axis of the graphs in FIGS. 11A and 11C corresponds to percentages of tumors in specific groups that have defined clinicopathological or molecular characteristics. This diagram shows correlations between clinical and histopathological characteristics of the tissue specimens in the micro-array. Each small box in the aligned rows of FIG. 11B represents a coordinate location in the array. Corresponding coordinates of consecutive thin sections of the recipient block are vertically aligned above one another in the horizontally extending rows. These results show that the tissue specimens could be classified into four classifications of tumors (FIG. 11A) based on the presence or absence of cell membrane estrogen receptor expression, and the presence or absence of the p53 mutation in the cellular DNA. In FIG. 11B, the presence of the p53 mutation is shown by a darkened box, while the presence of estrogen receptors is also shown by a darkened box. Categorization into each of four groups (ER−/p53+, ER−/p53−, ER+/p53+ and ER+/p53−) is shown by the dotted lines between FIGS. 11A and 11B, which divide the categories into Groups I, II, III and IV corresponding to the ER/p53 status.

FIG. 11B also shows clinical characteristics that were associated with the tissue at each respective coordinate of the array. A darkened box for Age indicates that the patient is premenopausal, a darkened box N indicates the presence of metastatic disease in the regional lymph nodes, a darkened box T indicates a stage 3 or 4 tumor which is more clinically advanced, and a darkened box for grade indicates a high grade (at least grade III) tumor, which is associated with increased malignancy. The correlation of ER/p53 status can be performed by comparing the top four lines of clinical indicator boxes (Age, N, T, Grade) with the middle two lines of boxes (ER/p53 status). The results of this cross correlation are shown in the bar graph of FIG. 11A, where it can be seen that ER−/p53+ (Group I) tumors tend to be of higher grade than the other tumors, and had a particularly high frequency of myc amplification, while ER+/p53+ (Group III) tumors were more likely to have positive nodes at the time of surgical resection. The ER−/p53− (Group II) showed that the most common gene amplified in that group was erbB2. ER−/p53− (Group II) and ER+/p53− (Group IV) tumors, in contrast, were shown to have fewer indicators of severe disease, thus suggesting a correlation between the absence of the p53 mutation and a better prognosis.

This method was also used to analyze the copy numbers of several other major breast cancer oncogenes in the 372 arrayed primary breast cancer specimens in consecutive FISH experiments, and those results were used to ascertain correlations between the ER/p53 classifications and the expression of these other oncogenes. These results were obtained by using probes for each of the separate oncogenes, in successive sections of the recipient block, and comparing the results at corresponding coordinates of the array. In FIG. 11B, a positive result for the amplification of the specific oncogene or marker (mybL2, 20q13, 17q23, myc, cnd1 and erbB2) is indicated by a darkened box. The erbB2 oncogene was amplified in 18% of the 372 arrayed specimens, myc in 25% and cyclin D1 (cnd1) in 24% of the tumors.

The two recently discovered novel regions of frequent DNA amplification in breast cancer, 17q23 and 20q13, were found to be amplified in 13% and 6% of the tumors, respectively. The oncogene mybL2 (which was recently localized to 20q13.1 and found to be overexpressed in breast cancer cell lines) was found to be amplified in 7% of the same set of tumors. MybL2 was amplified in tumors with normal copy number of the main 20q13 locus, indicating that it may define an independently selected region of amplification at 20q. Dotted lines between FIGS. 11B and 11C again divide the complex co-amplification patterns of these genes into Groups I-IV which correspond to ER−/p53+, ER−/p53−, ER+/p53+ and ER+/p53−.

FIGS. 11C and 11D show that 70% of the ER−/p53+ specimens were positive for one or more of these oncogenes, and that myc was the predominant oncogene amplified in this group. In contrast, only 43% of the specimens in the ER+/p53− group showed co-amplification of one of these oncogenes, and this information could in turn be correlated with the clinical parameters shown in FIG. 11A. Hence the microarray technology of the present invention permits a large number of tumor specimens to be conveniently and rapidly screened for these many characteristics, and analyzed for patterns of gene expression that may be related to the clinical presentation of the patient and the molecular evolution of the disease. In the absence of the microarray technology of the present invention, these correlations are more difficult to obtain.

Figure 12:
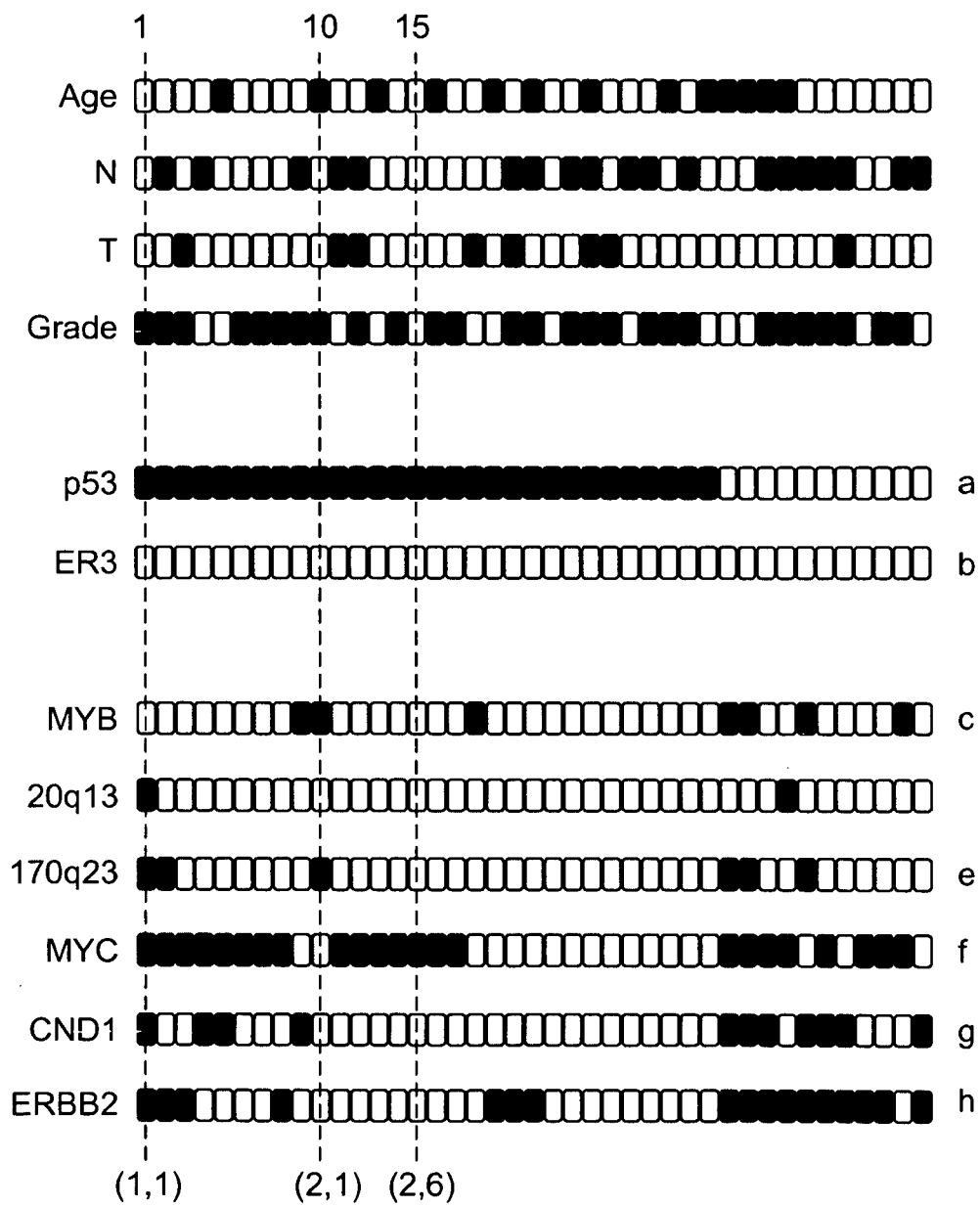
FIG. 12 is an enlarged view of a portion of FIG. 11.

A specific method of obtaining these correlations is illustrated in FIG. 12, which is an enlargement of the right hand portion of FIG. 11B. The microarray 76 (FIG. 10A) is arranged in sections that contain seventeen rows and nine columns of circular locations that correspond to cross-sections of cylindrical tissue specimens from different tumors, wherein each location in the microarray can be represented by the coordinates (row, column). For example, the specimens in the first row of the first section have coordinate positions (1,1), (1,2) ... (1,9), and the specimens in the second row have coordinate positions (2,1), (2,2), ..., (2,9). Each of these array coordinates can be used to locate tissue specimens from corresponding positions on sequential sections of the recipient block, to identify tissue specimens of the array that were cut from the same tissue cylinder.

FIG. 12 illustrates one conceptual approach to organizing and analyzing the array, in which the rectangular array may be converted into a linear representation in which each box of the linear representation corresponds to a coordinate position of the array. Each of the lines of boxes may be aligned so that each box that corresponds to an identical array coordinate position is located above other boxes from the same coordinate position. Hence the boxes connected by dotted line 1 correspond to the results that can be obtained by looking at the results at a coordinate position [for example (1,1)] in successive thin sections of the donor block, or clinical data that may not have been obtained from the microarray, but which can be entered into the system to further identify tissue from a tumor that corresponds to that coordinate position. Similarly, the boxes connected by dotted line 10 correspond to the results that can be found at coordinate position (2,1) of the array, and the boxes connected by dotted line 15 correspond to the results at coordinate position (2,6) of the array. The letters a, b, c, d, e, f, g, and h correspond to successive sections of the donor block that are cut to form the array.

By comparing the aligned boxes along line 1 in FIG. 12, it can be seen that a tumor was obtained from a postmenopausal woman with no metastatic disease in her lymph nodes at the time of surgical resection, in which the tumor was less than stage 3, but in which the histology of the tumor was at least Grade III. A tissue block was taken from this tumor and is associated with the recipient array at coordinate position (1,1). This array position was sectioned into eight parallel sections (a, b, c, d, e, f, g, and h) each of which contained a representative section of the cylindrical array. Each of these sections was analyzed with a different probe specific for a particular molecular attribute. In section a, the results indicated that this tissue specimen was p53+; in section b that it was ER−; in section c that it did not show amplification of the mybL2 oncogene; in separate sections d, e, f, g and h that it was positive for the amplification of 20q13, 17q23, myc, cnd1 and erbB2.

Similar comparisons of molecular characteristics of the tumor specimen cylinder that was placed at coordinate position (2,1) can be made by following vertical line 10 in FIG. 12, which connects the tenth box in each line, and corresponds to the second row, first column (2,1) of the array 76 in FIG. 10(A). Similarly the characteristics of the sections of the tumor specimen cylinder at coordinate position (2,6) can be analyzed by following vertical line 15 down through the $15^{th}$ box of each row. In this manner, parallel information about the separate sections of the array can be performed for all 372 positions of the array. This information can be presented visually for analysis as in FIG. 12, or entered into a database for analysis and correlation of different molecular characteristics (such as patterns of oncogene amplification, and the correspondence of those patterns of amplification to clinical presentation of the tumor).

Analysis of consecutive sections from the tumor arrays enables co-localization of hundreds of different DNA, RNA, protein or other targets in the same cell populations in morphologically defined regions of every tumor, which facilitates construction of a database of a large number of correlated genotypic or phenotypic characteristics of uncultured human tumors. Scoring of mRNA in situ hybridizations or protein immunohistochemical staining is also facilitated with tumor tissue microarrays, because hundreds of specimens can be analyzed in a single experiment. The tumor arrays also substantially reduce tissue consumption, reagent use, and workload when compared with processing individual conventional specimens one at a time for sectioning, staining and scoring. The combined analysis of several DNA, RNA and protein targets provides a powerful means for stratification of tumor specimens by virtue of their molecular characteristics. Such patterns will be helpful to detect previously unappreciated but important molecular features of the tumors that may turn out to have diagnostic or prognostic utility.

Analysis techniques for observing and scoring the experiments performed on tissue array sections include a brightfield microscope, fluorescent microscope, confocal microscope, a digital imaging system based on a CCD camera, or a photomultiplier or a scanner, such as those used in the DNA chip based analyses.

These results show that the very small cylinders used to prepare tissue arrays can in most cases provide accurate information, especially when the site for tissue sampling from the donor block is selected to contain histological structures that are most representative of tumor regions. It is also possible to collect samples from multiple histologically defined regions in a single donor tissue block to obtain a more comprehensive representation of the original tissue, and to directly analyze the correlation between phenotype (tissue morphology) and genotype. For example, an array could be constructed to include hundreds of tissues representing different stages of breast cancer progression (e.g. normal tissue, hyperplasia, atypical hyperplasia, intraductal cancer, invasive and metastatic cancer). The tissue array technology would then be used to analyze the molecular events that correspond to tumor progression.

A tighter packing of cylinders, and a larger recipient block can also provide an even higher number of specimens per array. Entire archives from pathology laboratories can be placed in replicate 500-1000 specimen tissue microarrays for molecular profiling. Using automation of the procedure for sampling and arraying, it is possible to make dozens of replicate tumor arrays, each providing hundreds of sections for molecular analyses. The same strategy and instrumentation developed for tumor arrays also enables the use of tissue cylinders for isolation of high-molecular weight RNA and DNA from optimally fixed, morphologically defined tumor tissue elements, thereby allowing correlated analysis of the same tumors by molecular biological techniques (such as PCR-based techniques)-based on RNA and DNA. When nucleic acid analysis is planned, the tissue specimen is preferably fixed (before embedding in paraffin) in an alcohol based fixative, such as ethanol or Molecular Biology Fixative (Streck Laboratories, Inc., Omaha, Nebr.) instead of in formalin, because formalin can cross-link and otherwise damage nucleic acid. The tissue cylinder of the present invention provides an ample amount of DNA or RNA on which to perform a variety of molecular analyses.

The potential of this array technology has been illustrated in FISH analysis of gene amplifications in breast cancer. FISH is an excellent method for visualization and accurate detection of genetic rearrangements (amplifications, deletions or translocations) in individual, morphologically defined cells. The combined tumor array technology allows FISH to become a powerful, high-throughput method that permits the analysis of hundreds of specimens per day.

Automated high speed devices can also be used that incorporate the basic principles of the device described herein. Such devices can process multiple donor and recipient trays or containers, and are described in Provisional Application Ser. No. 60/106,038 and PCT Application US99/04000, which are incorporated herein by reference. The devices are controlled by standard operating environments including a computer that comprises at least one high speed processing unit (CPU), in conjunction with a memory system, an input device, and one or more output devices. These elements are interconnected by at least one bus structure. The CPU is of familiar design and includes an ALU for performing computations, a collection of registers for temporary storage of data and instructions, and a control unit for controlling operation of the system. The CPU may be a processor having any of a variety of architectures including Alpha from Digital; MIPS from MIPS Technology, NEC, IDT, Siemens and others; x86 from Intel and others, including Cyrix, AMD, and Nexgen; 680x0 from Motorola; and PowerPC from IBM and Motorola. For example, the invention could be implemented with a Power Macintosh 8500 available from Apple Computer, or an IBM compatible Personal Computer (PC).

Examples and Applications of Array Technologies

The automated tumor array technology easily allows testing of dozens or hundreds of markers from the same set of tumors. These studies can be carried out in a multi-center setting by sending replicate tumor array blocks or sections to other laboratories. The same approach would be particularly valuable for testing newly discovered molecular markers for their diagnostic, prognostic, or therapeutic utility. The tissue array technology also facilitates basic cancer research by providing a platform for rapid profiling of hundreds or thousands of tumors at the DNA, RNA, and protein levels, leading to a construction of a correlated database of biomarkers from a large collection of tumors. For example, search for amplification target genes requires correlated analyses of amplification and expression of dozens of candidate genes and loci in the same cell populations. Such extensive molecular analyses of a defined large series of tumors would be difficult to carry out with conventional technologies.

Applications of the tissue array technology are not limited to studies of cancer, although the following Examples 1-4 disclose embodiments of its use in connection with analysis of neoplasms. Array analysis could also be instrumental in understanding expression and dosage of multiple genes in other diseases, as well as in normal human or animal tissues, including tissues from different transgenic animals or cultured cells.

Tissue arrays can also be used to perform further analysis on genes and targets discovered from, for example, high-throughput genomics, such as DNA sequencing, DNA microarrays, or SAGE (Serial Analysis of Gene Expression) (Velculescu et al., Science, 270:484-487, 1995). Tissue arrays can also be used to evaluate reagents for cancer diagnostics, for instance specific antibodies or probes that react with certain tissues at different stages of cancer development, and to follow progression of genetic changes both in the same and in different cancer types, or in diseases other than cancer. Tissue arrays can be used to identify and analyze prognostic markers or markers that predict therapy outcome for cancers. Tissue arrays compiled from hundreds of cancers derived from patients with known outcomes permit one or more of DNA, RNA, and protein assays to be performed on those arrays, to determine important prognostic markers, or markers predicting therapy outcome.

Tissue arrays can also be used to help assess optimal therapy for particular patients showing particular tumor marker profiles. For example, an array of tumors can be analyzed to determine which ones amplify and/or overexpress HER-2, such that the tumor type (or more specifically the subject from whom the tumor was taken) would be a good candidate for anti-HER-2 Herceptin immunotherapy. In another application, tissue arrays can be used to find novel targets for gene therapy. For example, cDNA hybridization patterns (such as on a DNA chip) may reveal differential gene regulation in a tumor of a particular tissue type (such as lung cancer), or a particular histological sub-type of the particular tumor (such as adenocarcinoma of the lung). Analysis of each of such gene candidates on a large tissue array containing hundreds of tumors would help determine which is the most promising target for developing diagnostic, prognostic, or therapeutic approaches for cancer.

EXAMPLES

The invention is further described in the following examples, which do not limit the scope of the invention described in the claims.

Example 1

Tissue Specimens

A total of 645 breast cancer specimens were used for construction of a breast cancer tumor tissue microarray. The samples included 372 fresh-frozen ethanol-fixed tumors, as well as 273 formalin-fixed breast cancers, normal tissues and fixation controls. The subset of frozen breast cancer samples was selected at random from the tumor bank of the institute of Pathology, University of Basel, which includes more than 1500 frozen breast cancers obtained by surgical resections during 1986-1997. Only the tumors from this tumor bank were used for molecular analyses. This subset was reviewed by a pathologist, who determined that the specimens included 259 ductal, 52 lobular, 9 medullary, 6 mucinous, 3 cribriform, 3 tubular, 2 papillary, 1 histiocytic, 1 clear cell, and 1 lipid rich carcinoma. There were also 15 ductal carcinomas in situ, 2 carcinosarcomas, 4 primary carcinomas that had received chemotherapy before surgery, 8 recurrent tumors and 6 metastases.

Histological grading was performed only in invasive primary tumors that had not undergone previous chemotherapy. Of these tumors, 24% were grade 1, 40% grade 2, and 36% grade 3. The pT stage was pT1 in 29%, pT2 in 54%, pT3 in 9%, and pT4 in 8%. Axillary lymph nodes had been examined in 282 patients (45% pN0, 46% pN1, 9% pN2). All previously unfixed tumors were fixed in cold ethanol at +4° C. overnight and then embedded in paraffin.

Example 2

Immunohistochemistry

After formation of the tissue array and sectioning of the donor block, standard indirect immunoperoxidase procedures were used for immunohistochemistry (ABC-Elite, Vector Laboratories). Monoclonal antibodies from DAKO (Glostrup, Denmark) were used for detection of p53 (DO-7, mouse, 1:200), erbB-2 (c-erbB-2, rabbit, 1:4000), and estrogen receptor (ER ID5, mouse, 1:400). A microwave pretreatment was performed for p53 (30 minutes at 90° C.) and erbB-2 antigen (60 minutes at 90° C.) retrieval. Diaminobenzidine was used as a chromogen. Tumors with known positivity were used as positive controls. The primary antibody was omitted for negative controls. Tumors were considered positive for ER or p53 if an unequivocal nuclear positivity was seen in at least 10% of tumor cells. The erbB-2 staining was subjectively graded into 3 groups: negative (no staining), weakly positive (weak membranous positivity), strongly positive (strong membranous positivity).

Example 3

Fluorescent In Situ Hybridization (FISH)

Two-color FISH hybridizations were performed using Spectrum-Orange labeled cyclin D1, myc, or erbB2 probes together with corresponding FITC labeled centromeric reference probes (Vysis). One-color FISH hybridizations were done with spectrum orange-labeled 20q13 minimal common region (Vysis, and see Tanner et al., *Cancer Res.* 54:4257-4260 (1994)), mybL2 and 17q23 probes (Barlund et al., *Genes Chrom. Cancer* 20:372-376 (1997)). Before hybridization, tumor array sections were deparaffinized, air dried and dehydrated in 70, 85, and 100% ethanol followed by denaturation for 5 minutes at 74° C. in 70% formamide-2× SSC solution. The hybridization mixture contained 30 ng of each of the probes and 15 µg of human Cot1-DNA. After overnight hybridization at 37° C. in a humidified chamber, slides were washed and counterstained with 0.2 µM DAPI in an antifade solution. FISH signals were scored with a Zeiss fluorescence microscope equipped with double-band pass filters for simultaneous visualization of FITC and Spectrum Orange signals. Over 10 FISH signals per cell or tight clusters of signals were considered as indicative of gene amplification.

Example 4 mRNA In Situ Hybridization

For mRNA in situ hybridization, tumor array sections were deparaffinized and air dried before hybridization. Synthetic oligonucleotide probes directed against erbB2 mRNA (Genbank accession number X03363, nucleotides 350-396) was labeled at the 3'-end with $^{33}$P-dATP using terminal deoxynucleotidyl transferase Sections were hybridized in a humidified chamber at 42° C. for 18 hours with $1 \times 10^7$ CPM/ml of the probe in 100 µL of hybridization mixture (50% formamide, 10% dextran sulfate, 1% sarkosyl, 0.02 M sodium phosphate, pH 7.0, 4×SSC, 1×Denhardt's solution and 10 mg/ml ssDNA). After hybridization, sections were washed several times in 1×SSC at 55° C. to remove unbound probe, and briefly dehydrated. Sections were exposed for three days to phosphorimager screens to visualize ERBB2 mRNA expression. Negative control sections were treated with RNase prior to hybridization, which abolished all hybridization signals.

The present method enables high throughput analysis of hundreds of specimens per array. This technology therefore provides an order of magnitude increase in the number of specimens that can be analyzed, as compared to prior blocks where a few dozen individual formalin-fixed specimens are in a less defined or undefined configuration, and used for antibody testing. Further advantages of the present invention include negligible destruction of the original tissue blocks, and an optimized fixation protocol which expands the utility of this technique to visualization of DNA and RNA targets. The present method also permits improved procurement and distribution of human tumor tissues for research purposes. Entire archives of tens of thousands of existing formalin-fixed tissues from pathology laboratories can be placed in a few dozen high-density tissue microarrays to survey many kinds of tumor types, as well as different stages of tumor progression. The tumor array strategy also allows testing of dozens or even hundreds of potential prognostic or diagnostic molecular markers from the same set of tumors. Alternatively, the cylindrical tissue samples provide specimens that can be used to isolate DNA and RNA for molecular analysis.

Example 5

Tissue Microarrays for Gene Amplification Surveys in Many Different Tumor Types

To facilitate rapid screening for molecular alterations in many different malignancies, a tissue microarray consisting of samples from 17 different tumor types, from 397 individual tumors, were arrayed in a single paraffin-block. Amplification of three oncogenes (CCND1, MYC, ERBB2) was analyzed in three Fluorescence in situ Hybridization (FISH) experiments from consecutive sections cut from the tissue microarray. Amplification of CCND1 was found in breast, lung, head and neck, and bladder cancer as well as in melanoma. ERBB2 was amplified in bladder, breast, colon, stomach, testis, and lung cancers. MYC was amplified in breast, colon, kidney, lung, ovary, bladder, head and neck, and endometrial cancer.

The microarray was constructed from a total of 417 tissue samples consisting of 397 primary tumors from 17 different tumor types and 20 normal tissues which were snap-frozen and stored at −70° C. Specimens were fixed in cold ethanol (+4° C.) for 16 hours and then embedded in paraffin. An H&E-stained section was made from each block to define representative tumor regions. Tissue cylinders with a diameter of 0.6 mm were then punched from tumor areas of each "donor" tissue block and brought into a recipient paraffin block using a custom-made precision instrument as described. Then 5 µm sections of the resulting multi-tumor tissue microarray block were transferred to glass slides using the paraffin sectioning aid system (adhesive coated slides, (PSA-CS4x), adhesive tape, UV-lamp; Instrumedics Inc., New Jersey) supporting the cohesion of 0.6 mm array elements.

The primary tumors consisted of 96 breast tumors (41 ductal, 28 lobular, 6 medullar, 5 mucinous, and 4 tubular carcinomas, 7 ductal carcinomas in situ (DCIS) and 5 phylloides tumors), 80 carcinomas of the lung (31 squamous, 11 large cell, 2 small cell, 31 adeno, and 5 bronchioloalveolar carcinomas), 17 head and neck tumors (12 squamous cell carcinomas of the oral cavity and 5 of the larynx), 32 adenocarcinomas of the colon, 4 carcinoids (3 from the lung and one from the small intestine), 12 adenocarcinomas from the stomach, 28 clear cell renal cell carcinomas, 20 testicular tumors (10 seminomas and 10 terato-carcinomas), 37 transitional cell carcinomas of the urinary bladder (33 invasive (pT1-4) and 4 non-invasive tumors), 22 prostate cancers, 26 carcinomas of the ovary (12 serous, 12 endometroid, and 2 mucinous tumors), 13 carcinomas from the endometrium, 3 carcinomas of the thyroid gland, 3 pheochromocytomas, and 4 melanomas. Normal tissue from breast, prostate, pancreas, small bowel, stomach, salivary gland, colon, and kidney were used as controls.

The tissue microarray sections were treated according to the Paraffin Pretreatment Reagent Kit protocol (Vysis, Ill.) before hybridization. FISH was performed with Spectrum Orange-labeled CCND1, ERBB2, and MYC probes. Spectrum Green-labeled centromeric probes CEP11 and CEP17 were used as a reference (Vysis, Ill.). Hybridization and post-hybridization washes were according to the "LSI procedure" (Vysis, Ill.). Slides were then counterstained with 125 ng/ml 4',6-diamino-2-phenylindole in antifade solution. FISH signals were scored with a Zeiss fluorescence microscope equipped with double-band pass filters for simultaneous visualization of Spectrum Green and Spectrum Orange signals (Vysis, Ill.). Amplification was defined as presence (in at least 5% of tumor cells) of either (a) more than 10 gene signals or tight clusters of at least 5 gene signals; or (b) more than 3 times as many gene signals than centromere signals of the respective chromosome.

Seventy-two amplifications were found in 968 successfully hybridized tumor samples, whereas none of the normal tissues showed amplification. Amplification usually involved almost all tumor cells within an array element. CCND1 amplification was found in 6 of 16 head and neck carcinomas (38%), 14 of 62 breast carcinomas (23%), 1 of 6 DCIS (17%), 3 of 27 bladder cancers (11%), 7 of 76 carcinomas of the lung (9%), and 1 of 4 melanomas.

MYC amplification was observed in 2 of 11 endometrial cancers (18%), 9 of 74 breast carcinomas (12%), 1 of 5 DCIS (20%), 1 of 17 head and neck cancers (6%), 1 of 22 tumors of the kidney (5%), 2 of 24 ovarian carcinomas (8%), 1 of 17 tumors of the testis (6%), 1 of 30 colon carcinomas (3%), 7 of 78 lung tumors (9%), and in 1 of 33 bladder-tumors (3%).

ERBB2 was amplified in 4 of 71 breast carcinomas (6%), 4 of 6 DCIS (67%), 2 of 11 stomach cancers (18%), 1 of 30 colon carcinomas (3%), 1 of 17 tumors of the testis (6%) and in 1 of 75 carcinomas of the lung (1%). Co-amplifications of all three genes were seen in two breast carcinomas. Co-amplifications of two genes were found in two breast carcinomas (CCND1/MYC and CCND1/ERBB2) and in one terato-carcinoma of the testis (MYC and ERBB2).

Consecutive sections cut from the block provide starting material for the in situ detection of multiple DNA, RNA or protein targets in many tissues at a time, in a massively parallel fashion. The tissue array technology permits increased capacity, automation, negligible damage to the original tissue blocks from which the specimens are taken, the precise positioning of tissue specimens, and the use of these tissues in different kinds of molecular analyses, besides immunostaining. It is possible to retrieve 10-20 punched samples (or more) from each donor block without significantly damaging it. This enables generation of multiple replicate array blocks, each with the identical coordinates, and the same specimens. The application of a precision instrument to deposit the samples in a predefined format also facilitates the development of automated image analysis strategies for the arrayed tumors. Depending on the thickness of the original tissue blocks, between 150 and 300 sections can be cut from each array block. This technology enables analyses of even small primary tumors, thereby preserving often unique and precious tumor specimens for a large number of analyses that may be of interest in future investigations.

The array data reported in this example agreed with the previous literature on the presence or absence of gene amplification in 73% of evaluations, although the number of samples per tumor type was too small for a comprehensive analysis of some tumor types in this pilot study. Previously described amplifications were not detected on the array in 9 of 25 tumor types from which less than 25 samples were examined. In contrast, when at least 25 cases were analyzed per tumor type, 92% of the known amplifications (11/12) were detected.

In this study, frozen tumor tissues were fixed in cold ethanol because this procedure allows the retention of good quality nucleic acids from fixed tissue samples. Even formalin-fixed tumor tissues, such as those obtained at autopsy, can be analyzed by FISH for DNA copy number alterations. However, the cold ethanol fixation is advantageous for FISH, because the samples require ewer pretreatments than samples fixed in 4% buffered formalin. Cold ethanol fixation may cause RNAs to degrade in paraffin blocks after only a few months of storage, hence it may not be desired to fix a large series of precious tissues in cold ethanol, unless RNA inhibitors are added or blocks stored in a manner that prohibits this degradation.

Example 6

PDGFB FISH Experiments Using a Multi-Tumor Tissue Array

The multi-tumor tissue array of Example 5 was used in this experiment. A platelet-derived growth factor beta (PDGFB) probe was obtained from Vysis Inc. of Downers Grove, Ill. The probe was obtained by PCR screening of a genomic large-insert library using two sequence tagged sites (STS) in the gene sequence as a target for developing PCR primers that were used in the PCR-based library screening. The hits obtained from genomic library screening were further verified by their content of the STSs, as well as by hybridizing the probe to metaphase chromosomes using FISH. This resulted in a signal at the expected chromosomal location of PDGFB.

PCR/STS screening can be performed using a PCR primer set specific to the gene of interest, as described by Green & Olson, PNAS USA, 87:1213-1217, 1990. Probes for FISH may be generated from large-insert libraries (e.g., cosmids, P1 clones, BACs, and PACs) using a PCR-based screening of arrayed and pooled large-insert libraries. Both Research Genetics (Huntsville, Ala.) and Genome Systems (St. Louis) perform such filter screening, and sell pools of DNA for performing library screening.

One method of isolating the P1 clone for PDGFB (pVYS309A) would be to screen DNA pools of a human P1 library obtained from Genome Systems, Inc. Individual clones are identified by producing the expected DNA fragment size on gels after PCR. Bacterial cultures containing candidate PDGFB clones are purified by streaking on nutrient agar media for single colonies. Cultures from individual colonies are then grown and DNA isolated by standard techniques. The DNA is confirmed to contain the desired DNA sequence by PCR and gel electrophoresis (STS confirmation). A sample of the DNA is labeled by nick-translation or random priming with SpectrumOrange dUTP (Vysis) and shown to hybridize to the expected region of chromosome 22q normal metaphase chromosomes by FISH.

PCR primers for PDGFB can be derived from the published sequence of the cDNA of this gene (GenBank Accession X02811). The preferred region of STS design is the 3' untranslated region of the cDNA. Several PCR primer sets for PDGFB are in public databases, e.g., amplimers (PCR primer sets) PDGFB PCR1, PDGFB PCR2, PDGFB PCR3, stPDGFB.b, WI-8985, and can be found in the Genome Database (gdbwww.gdb.org/gdb/gdbtop-html). WI-8985 primer sets can also be found at the Whitehead Institute database (www-genome.wi.mit.edu/), and at the NIH Gene Map 98 database (www.ncbi.nlm.nih.gov/genemap98/).

FISH was done using standard protocols, as in Example 5, and hybridization of the probe to specimens of the tissue array was detected as in Example 5. Hybridization was detected in the following types of tumors:

| TUMOR | Ratio Positive | Percent Positive |
|---|---|---|
| breast CA | 2/70 | 2.9% |
| phylloides | 0/4 | |
| DCIS | 0/7 | |
| lung | 15/77 | 19% |
| colon | 1/30 | 3.3% |
| carcinoid | 0/3 | |
| stomach | 0/9 | |
| renal cell | 0/11 | |
| testis | 1/16 | 6% |
| TCC (bladder transitional cell carcinoma) | 10/32 | 31% |
| head/neck | 0/17 | |
| PCA | 0/18 | |
| ovary | 0/22 | |
| endometrium | 2/8 | 25% |
| Total | 22/324 | |

This Example provides the first evidence of previously unsuspected, high-level amplifications of PDGFB in specific types of malignancies, such as breast, lung, colon, testicular, endometrial, and bladder cancer.

Example 7

Gene Amplifications During Prostate Cancer Progression

In this study, five different gene amplifications (AR, CMYC, ERBB2, Cyclin D1, and NMYC) were assayed by FISH from consecutive formalin fixed tissue microarray sections containing samples from more than 300 different prostate tumors. The objective was to obtain a comprehensive survey of gene amplifications in different stages of prostate cancer progression, including specimens from distant metastases. The tissue microarray contained minute samples from 371 specimens.

Formalin-fixed and paraffin-embedded tumor and control specimens were obtained from the archives of the Institutes for Pathology, University of Basel (Switzerland) and the Tampere University Hospital (Finland). The least differentiated tumor area was selected to be sampled for the tissue microarray. The minute specimens that were interpretable for at least one FISH probe included: I) transurethral resections from 32 patients with benign prostatic hyperplasia (BPH) which were used as controls; II) 223 primary tumors, including 64 cancers incidentally detected in transurethral resections for BPH; stage T1a/b, 145 clinically localized cancers from radical prostatectomies, and 14 transurethral resections from patients with primary, locally extensive disease; III) 54 local recurrences after hormonal therapy failure including 31 transurethral resections from living patients and 23 specimens obtained from autopsies; IV) Sixty-two metastases collected at the autopsies from 47 patients who had undergone androgen deprivation by orchiectomy, and had subsequently died of end-stage metastatic prostate cancer. Metastatic tissue was sampled from pelvic lymph nodes (8), lung (21), liver (16), pleura (5), adrenal gland (5), kidney (2), mediastinal lymph nodes (1), peritoneum (i), stomach (1), and ureter (1). In 23 autopsies material was available from both the primary and from the metastatic site. More than one sample per tumor specimen was arrayed in 44 of the 339 cases. A tumor was considered amplified if at least one sample from the tumor exhibited gene amplification.

The array also included 48 pathologically representative samples which consistently failed in the analysis of sections with all FISH probes, and were therefore excluded from the analyses. Most of these were autopsy samples. The number of samples evaluated with the different probes was variable, because the hybridization efficiency of the probes was slightly different, some samples on the array were occasionally lost during the sectioning or FISH-procedure, and some tumors were only representative on the surface of the block, and she morphology changed as more sections were cut.

The prostate tissue microarray was constructed as previously described in Example 1, except with prostate instead of breast cancer specimens.

Two-color FISH to sections of the arrayed formalin-fixed samples was performed using Spectrum Orange-labeled AR, CMYC, ERBB2, and CyclinD1 (CCND1) probes with corresponding FITC-labeled centromeric probes (Vysis, Downer's Grove, Ill.). In addition, one-color FISH was done with a Spectrum Orange-labeled NMYC probe (Vysis). The hybridization was performed according to the manufacturer's instructions. To allow formalin-fixed tumors on the array to be reliably analyzed by FISH, the slides of the prostate microarray were first deparaffinized, acetylated in 0.2 N HCl, incubated in 1 M sodium thiocyanate solution at 80° C. for 30 minutes and immersed in a protease solution (0.5 mg/ml in 0.9% NaCl) (Vysis) for 10 minutes at 37° C. The slides were then post-fixed in 10% buffered formalin for 10 minutes, air dried, denatured for 5 minutes at 73° C. in 70% formamide/ 2×SSC(SSC is 0.3 M sodium chloride and 0.03 M sodium citrate) solution and dehydrated in 70, 80, and 100% ethanol, followed by proteinase K (4 µg/ml phosphate buffered saline) (GIBCOBRL, Life Technologies Inc., Rockville, Md.) treatment for 7 minutes at 37° C. The slides were then dehydrated and hybridized.

The hybridization mixture contained 3 µl of each of the probes and Cot1-DNA (1 mg/ml; GIBCOBRL, LifeTechnologies Inc., Rockville, Md.) in a hybridization mixture. After overnight hybridization at 37° C. in a humid chamber, slides were washed, and counterstained with 0.2 µM DAPI. FISH signals were scored with a Zeiss fluorescence microscope equipped with a double-band pass filter using ×40-×100 objectives. The relative number of gene signals in relation to the centromeric signals was evaluated. Criteria for gene amplification were: at least 3 times more test probe signals than centromeric signals per cell in at least 10% of the tumor cells. Test/control signal ratios in the range between 1 and 3 were regarded as low level gains, and were not scored as evidence of specific gene amplification. Amplification of NMYC without a reference probe was defined as at least 5 gene signals in at least 10% of the tumor cells.

High-quality hybridization signals with both centromeric and gene specific probes were obtained in 96% of the BPH samples for chromosome X/AR gene, 84% for chromosome 8/CMYC, 81% for chromosome 17/ERBB2, and 83% for chromosome 11/Cyclin D1. In the BPH samples that could be evaluated, the average percentage of epithelial cells with two signals for autosomal probes was ~75%, with ~20% showing one signal, and ~5% no signals. The percentage of cells with one or zero signals is believed to be attributable to the truncation of nuclei with sectioning. In the punched (single array element) samples of biopsy cancer specimens, AR, CMYC, ERBB2, and CCND1 FISH data could be obtained from 92%, 78%, 82%, and 86% of the cases, respectively. The success rate of FISH was lower in punches from autopsy tumors (44-58%). Amplifications were only scored when the copy number of the test probe exceeded that of the chromosome-specific centromere reference probe by ≥3-fold in 10% or more of the tumor cells. This criterion was chosen, as low-level amplification is likely to be less relevant, and since locus-specific probes often display slightly higher copy numbers than centromeric probes, due to signal splitting or the presence of G2/M-phase cells.

FISH with the AR probe revealed amplification in 23.4% of the 47 evaluable hormone-refractory local recurrences. Amplification was seen equally often (22.0%) in 59 metastases of hormone-refractory tumors. The strong association between AR amplification and hormone-refractory prostate cancer is evident from the fact that only two of the 205 evaluable primary tumors (1%) and none of the 32 BPH controls showed any AR amplification. The two exceptions included a patient with locally advanced and metastatic prostate cancer, and another patient with clinically localized disease. Paired tumors from the primary site of the cancer and from a distant metastasis of 17 patients were successfully analyzed for AR amplification. In 11 of these patients, no AR amplification could be seen at either site. Of the six remaining patients, three patients showed amplification both in the local tumor mass, as well as in the distant metastases. In two cases amplification was only found in the sample from the primary site, whereas in another case only the distant metastasis showed amplification.

High-level CMYC amplifications were found in 5 of 47 evaluable metastatic deposits (10.6%), in 2 of the 47 local recurrences (4.3%, both metastatic cancers), but in none of the 168 evaluable primary cancers or 31 BPH controls. The comparison between different gene amplifications within the tumor cells defined by single punch-samples (array elements) showed that there was a significant association between AR and CMYC amplifications CMYC was amplified in 11.1% of 27 evaluable punch-samples with AR amplifications but only in 1.7% of 235 samples without AR amplifications (p=0.0041, contingency table analysis). AR was independently amplified in 24 samples, whereas only four samples had CMYC amplification, but no AR amplification.

On a tumor by tumor basis, there was a significant association between AR and CMYC amplifications. CMYC was amplified in 12.5% of 24 evaluable tumors with AR amplifications, but only in 1.8% of 219 tumors without AR amplifications (p=0.003, contingency table analysis). AR was independently amplified in 21 tumors, whereas only 4 tumors had CMYC amplification, but no AR amplification.

CCND1 amplifications were found in 2 (1.2%) of the 172 evaluable primary tumors, in 3 (7.9%) of 38 local recurrences, and in 2 (4.7%) of the 43 metastases. CCND1 amplification appeared independent from AR or CMYC amplification with 4/7 CCND1 amplified punched tumor samples not showing amplifications for any other genes tested. There were no ERBB2 amplifications among any of the 262 evaluable tumors or 31 BPH controls. Finally, a subset of the tumors was analyzed with the NMYC probe in a single color FISH analysis. Out of the 164 tumors available, none showed amplification, as defined by the lack of 5 or more signals per cell in >10% of the tumor cells.

For this study a tumor array was constructed that allowed investigation of the pattern of amplifications of multiple genes in samples representing the entire spectrum of prostate cancer progression, including distant metastases. The tumor array strategy facilitates standardized analysis of multiple genes in the same tumors, even in the same specific tumor sites using the same technology, with the same kind of probes, and similar interpretation criteria. In just five FISH experiments, 371 specimens were screened for five genes resulting in a total of over 1400 evaluable FISH results. The ability to achieve reliable detection of gene amplifications from formalin-fixed tissues substantially extends the range of possible applications for the tumor array technology.

Many symptomatic prostate cancers become both hormone-refractory and metastatic, and it is difficult to distinguish between these two clinical features, or the molecular mechanisms that contribute to either of these processes. The results of the present example indicate that AR amplification is more closely associated with the development of hormone-refractory cell growth, whereas CMYC amplification is associated with metastatic progression. The most common gene amplification in prostate cancers is that of the AR gene, which is usually amplified independently of both CMYC and Cyclin D1. In this study, CMYC amplifications were more common in the distant metastases (11%) than in the locally recurrent tissues (4%; both from patients with end-stage metastatic cancers), whereas AR amplifications were equally common at both anatomical sites (22% and 23%, respectively). This suggests that AR is conferring an advantage for hormone-refractory growth, and not metastatic dissemination, whereas the reverse may be true for CMYC.

This Example indicates that the AR gene is the most frequent target, and often the first target, selected for amplification during prostate cancer progression. Second, in contrast to AR, amplifications of the CMYC oncogene appear to be primarily associated with metastatic dissemination. Finally, prostate cancers occasionally also amplify the Cyclin D1 gene, whereas ERBB2 and NMYC amplifications are unlikely to play a significant role at any stage of the progression of prostate cancer.

Example 8

Rapid Screening for Prognostic Markers in Renal Cell Carcinomas (RCC) by Combining cDNA-Array and Tumor-Array Technologies This example first uses cDNA arrays to identify genes that play a role in renal cell carcinoma (RCC), and subsequently analyzes emerging candidate genes on a tumor array for their potential clinical significance. The results show that the combination of nucleic acid arrays and tumor arrays is a powerful approach to rapidly identify and further evaluate genes that play a role in RCC biology.

cDNA was synthesized and radioactively labeled using 50 μg of total RNA from normal kidney (Invitrogen) and a renal cancer cell line (CRL-1933) (ATCC, VA, USA) according to standardized protocols (Research Genetics; Huntsville, Ala.). Release I of the human GeneFilters from Research Genetics was used for differential expression screening. A single membrane contained 5184 spots each representing 5 ng of cDNA of known genes or expressed sequence tags (EST's). After separate hybridization the two cDNA array filters (Research Genetics) were exposed to a high resolution screen (Packard) for three days. The gene expression pattern of 5184 genes in normal tissue and the tumor cell line was analyzed and compared on a phosphor imager (Cyclone, Packard). To define genes/EST's as under- or overexpressed, both an at least tenfold expression difference between normal tissue and the cell line using the Pathfinder software (Research Genetics; Huntsville, Ala.) and visual confirmation of an unequivocal difference in the staining intensity on filters was requested.

For the construction of the renal tumor microarray block, a collection of 615 renal tumors after nephrectomy was screened for availability of representative paraffin-embedded tissue specimens Tumor specimens from 532 renal tumors and tissue from 6 normal kidneys were selected for the tumor array. The tumors were staged according to TNM classification, graded according to Thoenes (*Pathol. Res. Pract.,* 181: 125-143, 1986) and histologically subtyped according to the recommendations of the UICC (Bostwick et al., *Cancer,* 80:973-1001, 1997) by one pathologist. Core-tissue-biopsies (diameter 0.6 mm) were taken from selected morphologically representative regions of individual paraffin-embedded renal tumors (donor blocks) and precisely arrayed into a new recipient paraffin block (45 mm×20 mm) using a custom-built instrument. Then 5 μm sections of the resulting tumor tissue micro array block were transferred to glass slides using the paraffin sectioning aid system (adhesive coated slides, (PSA-CS4x), adhesive tape, UV-lamp; Instrumedics Inc., New Jersey) supporting the cohesion of 0.6 mm array elements.

Standard indirect immunoperoxidase procedures were used for immunohistochemistry (ABC-Elite, Vectra Laboratories) as described, for example in Moch et al., *Hum. Pathol.,* 28:1255-1259, 1997. A monoclonal antibody was employed for vimentin detection (anti-vimentin; Boehringer Mannheim, Germany, 1:160). Tumors were considered positive for vimentin, if an unequivocal cytoplasmic positivity was seen in tumor cells. Vimentin positivity in endothelial cells served as an internal control. The vimentin positivity in epithelial cells was defined as negative (no staining) or positive (any cytoplasmic staining).

Contingency table analysis was used to analyze the relationship between vimentin expression, grade, stage, and tumor type. Overall survival was defined as the time between nephrectomy and patient death. Survival rates were plotted using the Kaplan-Meier method. Survival differences between the groups were determined with the log-rank test. A Cox proportional hazard analysis was used to test for independent prognostic information.

Two cDNA array membranes were hybridized with radioactive-labeled cDNA from normal kidney and tumor cell line CRL-1933. The experiment resulted in 89 differentially expressed genes/EST's. An overexpression in CRL-1933 was found for 38 sequences, including 26 named genes and 12 EST's while 51 sequences (25 named genes, 26 EST's) were underexpressed in the cell line. The sequence of one of the upregulated genes in the cell line was identical to vimentin.

The presence of epithelial tumor cells was tested for every tissue cylinder using an H&E-stained slide. Vimentin expression could be evaluated on the tissue cylinders in 483 tumors and all 6 normal kidney tissues. Vimentin expression was frequent in clear-cell (51%) and papillary RCC (61%), but rare in 23 chromophobe RCC (4%). Only 2 of 17 oncocytomas showed a weak vimentin expression (12%). Normal renal tubules did not express vimentin. The association between vimentin expression and histological grade and tumor stage was only evaluated for clear cell RCC. Vimentin expression was more frequent in grade II (44%) and grade III (42%) than in grade I (13%) RCC ($p<0.0001$). Vimentin expression was more common in higher tumor stages (60% in stage pT1/2 versus 40% in stage pT3/4), but this difference was not significant ($p=0.09$).

There was a mean follow-up of 52.9±51.4 months (median, 37, minimum 0.1, maximum 241 months). Poor overall survival was strongly related to high histologic grade ($p<0.0001$) and high tumor stage ($p<0.0001$). The association between patient prognosis and vimentin expression was evaluated for patients with clear cell RCC. Vimentin expression was strongly associated with short overall survival ($p=0.007$). Proportional Hazards analysis with the variables tumor stage, histological grade, and vimentin expression indicates that vimentin expression was an independent predictor of prognosis, the relative risk being 1.6 ($p=0.01$) in clear cell RCC.

The results of this example show that the combination of cDNA and tumor arrays is a powerful approach for identification and further evaluation of genes playing a role in human malignancies. This example illustrates that cDNA arrays may be used to search for genes that are differentially expressed in tumor cells (such as kidney cancer) as compared to normal tissue (kidney tissue in this example). Evaluation of all candidate genes emerging from a cDNA experiment on a representative set of uncultured primary tumors would take years if traditional methods of molecular pathology were used. However the tumor microarray technology markedly facilitates such studies. Tissue arrays allow the simultaneous in situ analysis of hundreds of tumors on the DNA, RNA and protein level, and even permits correlation with clinical follow up data.

This high throughput analysis allowed marked differences in the vimentin expression between renal tumor subtypes to be illustrated. Vimentin was frequently detected in papillary and clear cell RCC, but rarely in oncocytoma and chromophobe RCC. Given the high rate of vimentin positivity in clear cell RCC detected in this example, the presence of vimentin expression may be used as a diagnostic feature to distinguish a diagnosis of clear cell RCC from chromophobe RCC.

This example further illustrates that tumor tissue arrays can facilitate the translation of findings from basic research into clinical applications. The speed of analysis permits a multi-step strategy. First, molecular markers or genes of interest are assessed on a master multi-tumor-array containing samples of many (or all) possible human tumor type. In a second step, all tumor types that have shown alterations in the initial experiment are then further examined on tumor type-specific arrays (for example bladder cancer) containing much higher numbers of tumors of the same tissue type, with clinical follow up information on survival or response to specific therapies. In a third step the analysis of conventional (large) diagnostic histologic and cytologic specimens is then restricted to those markers for which promising data emerged during the initial array based analyses. For example, vimentin expression can now be studied on larger tissue specimens to confirm its prognostic significance in clear cell RCC. If the array data are confirmed, vimentin immunohistochemistry may then be included in prospective studies investigating prognostic markers in RCC.

Example 9

DNA Array Technology

Instead of using a single probe to test for a specific sequence on the sample DNA, a gene or DNA chip incorporates many different "probes." Although a "probe" usually refers to what is being labeled and hybridized to a target, in this situation the probes are attached to a substrate. Many copies of a single type of probe are bound to the chip surface in a small spot which may be, for example, approximately 0.1 mm or less in diameter. The probe may be of many types including DNA, RNA, cDNA, or oligonucleotide. In variations of the technology, specific proteins, polypeptides or immunoglobulins or other natural or synthetic molecules may be used as a target for analyzing DNA, RNA, protein or other constituents of cells, tissues, or other biological specimens. Many spots, each containing a different molecular target, are then arrayed in the shape of a grid. The surface for arraying may be a glass, or other solid material, or a filter paper or other related substance useful for attaching biomolecules. When interrogated with labeled sample, the chip indicates the presence or absence of many different sequences or molecules in that specimen. For example, a labeled cDNA isolated from a tissue can be applied on a DNA chip to assay for expression of many different genes at a time.

The power of these chips resides not only in the number of different sequences or other biomolecules that can be probed simultaneously, as explained below for nucleic acid chips. In the analysis of nucleic acids, a relatively small amount of sample nucleic acid is required for such an analysis (typically less than a millionth of a gram of nucleic acid). The binding of nucleic acid to the chip can be visualized by first labeling the sample nucleic acid with fluorescent molecules or a radioactive label. The emitted fluorescent light or radioactivity can be detected by very sensitive cameras, confocal scanners, image analysis devices, radioactive film or a PHOSPHOIMAGER™, which capture the signals (such as the color image) from the chip. A computer with image analysis software detects this image, and analyzes the intensity of the signal for each probe location in the array. Detection of differential gene expression with a radioactive cDNA array was already described in Example 8. Usually, signals from a test array are compared with a reference (such as a normal sample).

DNA chips may vary significantly in their structure, composition, and intended functionality, but a common feature is usually the small size of the probe array, typically on the order of a square centimeter or less. Such an area is large enough to contain over 2,500 individual probe spots, if each spot has a diameter of 0.1 mm and spots are separated by 0.1 mm from each other. A two-fold reduction in spot diameter and separation can allow for 10,000 such spots in the same array, and an additional halving of these dimensions would allow for 40,000 spots. Using microfabrication technologies, such as photolithography, pioneered by the computer industry, spot sizes of less than 0.01 mm are feasible, potentially, providing for over a quarter of a million different probe sites.

Targets on the array may be made of oligomers or longer fragments of DNA. Oligomers, containing between 8 and 20 nucleotides, can be synthesized readily by chemical methods. Photolithographic techniques allow the synthesis of hundreds of thousands of different types of oligomers to be separated into individual spots on a single chip, in a process referred to as in situ synthesis. Long pieces of DNA, on the other hand, contain up to several thousand nucleotides, and can not be synthesized through chemical methods. Instead, they are excised from the human genome and inserted into bacterial cells through genetic engineering techniques. These cells, or clones, serve as a convenient source for these DNAs, which can be produced in large quantities by fermentation. After extraction and appropriate chemical preparation the DNA from each clone is deposited onto the chip by a robot, which is equipped either with very fine syringes or with an ink-jet system.

The targets on the DNA chip interact with the DNA that is being analyzed (the target DNA) by hybridizing. The specificity of this process (the accuracy with which the sample nucleic acid sequences will bind to their complementary arrayed target sequences) is mainly a function of the length of the probe. For short oligonucleotide probes, the conditions can be chosen such that a single point mutation (the change of a single nucleotide in a gene) can be detected. That may require as many as 65,536 or even more different oligonucleotide probes on a single chip to unambiguously deduce the sequence of even a relatively small DNA sequence. This process, called sequencing by hybridization (SbH), generates very complex hybridization patterns that are interpreted by image analysis computer software. In addition, the sequence to be analyzed is preferably short, and it must be isolated and amplified from the rest of the genome through a technique called Polymerase Chain Reaction (PCR), before it is applied to the chip for sequence analysis In Comparative Genomic Hybridization (CGH), DNA from a sample tissue, such as a tumor, is compared to normal human DNA. In a particular example of CGH performed by Vysis, Inc., this is accomplished by labeling the sample DNA with a fluorescent dye, and the reference ("normal") DNA with a fluorescent dye of a different color. Both DNAs are then mixed in equal amounts and hybridized to a DNA chip. The Vysis chip or genosensor, contains an array of large insert DNA clones, each comprising approximately 100,000 nucleotides of human DNA sequence. After hybridization, a multi-color imaging system determines the ratio of colors (for example green to red fluorescence) for each of the probe spots in the array. If there is no difference between the sample DNA and the normal DNA, then all spots should have an equal mixture of red and green fluorescence, resulting in a yellow color. A shift toward green or red for a given spot would indicate that either more green or more red labeled DNA was bound to the chip by that probe sequence. This color shift indicates a difference between the sample and the reference DNA for that particular region on the human genome, pointing either toward amplification or deletion of a specific sequence or gene contained in the clones positioned in the array. Examples of genetic changes that can be detected include amplifications of genes in cancer, or characteristic deletions in genetic syndromes, such as Cri du chat.

Since each genetic region to be analyzed needs to be represented on the chip in only 1 or few replicate spots, the genosensor can be designed to scan the total human genome for large deletions or duplications in a single assay. For example, an array of just 3000 different clones evenly spaced along the human genome would provide a level of resolution that is at least 10 times better than what can be achieved with metaphase hybridization, at a much lower cost and in much less time. Specialty chips can be tailored to the analysis of certain cancers or disease syndromes, and can also provide physicians with much more information on routine clinical analysis than currently can be obtained even by the most sophisticated research laboratories.

The color ratio analysis of the genosensor CGH (gCGH) assay has the advantage that absolute quantitation of the amount of a specific sequence in the sample DNA is not required. Instead, only the relative amount compared to the reference (normal) DNA is measured with relatively high accuracy. This approach is equally useful for a third kind of chip technology, referred to as "Expression Chips." These chips contain arrays of probe spots which are specific for different genes in the human genome. They do not measure the presence or absence of a mutation in the DNA directly, but rather determine the amount of message that is produced from a given gene. The message, or mRNA, is an intermediary molecule in the process by which the genetic information encoded in the DNA is translated into protein. The process by which mRNA amounts are measured involves an enzymatic step which converts the unstable mRNA into cDNA, and simultaneously incorporates a fluorescent label. cDNA from a sample tissue is labeled in one color and cDNA from a normal tissue is labeled with a different color. After comparative hybridization to the chip, a color ratio analysis of each probe spot reveals the relative amounts of that specific mRNA in the sample tissue compared to normal tissue. Expression chips measure the relative expression of each gene for which there is a probe spot on the chip.

There are approximately 100,000 different genes in the human genome, and it is expected that all of them will be known within a few years. Since chips with thousands of different probe spots can be made, the relative expression of each gene can be determined in a single assay. This has significant implications for disease diagnosis and therapy. Expression chips may be used to test the effect of drugs on the expression of a limited number of genes in tissue culture cells, by comparing mRNA from drug treated cells to that of untreated cells. The ability to measure the effect on the regulation of all genes will allow a much more rapid and precise drug design, since the potency and potential side effects of drugs can be tested early in development. Moreover, the rapid increase in understanding of the regulatory switches that determine tissue differentiation will allow for the design of drugs that can initiate or modify these processes. Findings about differential expression in CGH can be further analyzed in tissue arrays, in which expression of mRNA can also be determined.

In one particular embodiment of CGH, a DNA chip or genosensor (hence, genosensor CGH or gCGH), such as an AmpliOnc™ chip from Vysis, contains an array of P1, BAC, or PAC clones, each with an insert of human genomic DNA. The size of these inserts ranges from 80 to 150 kilobases, and they are spaced along the human genome to improve the resolution of this technique. Since the hybridization probe mixture contains only on the order of 200 ng of total human DNA from each of the test and reference tissue, the total number of available probes for each arrayed target clone is relatively low, placing higher demands on the sensitivity of this system than what is needed for regular fluorescent in situ hybridization techniques. These demands have been met with the development of improved chip surfaces, attachment chemistry, and imaging systems. The combination of such features can provide a sensitivity of <$10^8$ fluorophors/cm$^2$, which is achieved through highly efficient background reduction.

Autofluorescence emanating from the chip surface may be reduced by coating the glass chip with chromium, as disclosed in U.S. patent application Ser. No. 09/085,625. This highly reflective surface provides enhanced signal collection efficiency, and its hydrophobic nature reduces non-specific binding of probes. Efficient reading of CGH chips is achieved with a sensitive, high speed, compact, and easy to use multicolor fluorescence imaging system, such as that described in U.S. patent application Ser. No. 09/049,748. The non-epifluorescent excitation geometry eliminates autofluorescence from the collection optics, and collects only fluorescent light from the chip surface. A xenon arc lamp serves as a safe and long-lasting light source, providing even illumination over a wide range of wavelengths. This allows for the use of many different fluorophores, limited only by the choice of excitation and emission filters. Fluorescent images are acquired from a 14 mm×9 mm sample area by a cooled CCD camera without scanning or magnification, and even the need for routine focusing has been eliminated. The images are analyzed by software, which interrogates each individual pixel to calculate the ratio of sample to reference probe that are hybridized to each target spot. An appropriate statistical analysis reveals the relative concentration of each target specific sequence in the probe mixture.

Figure 13:
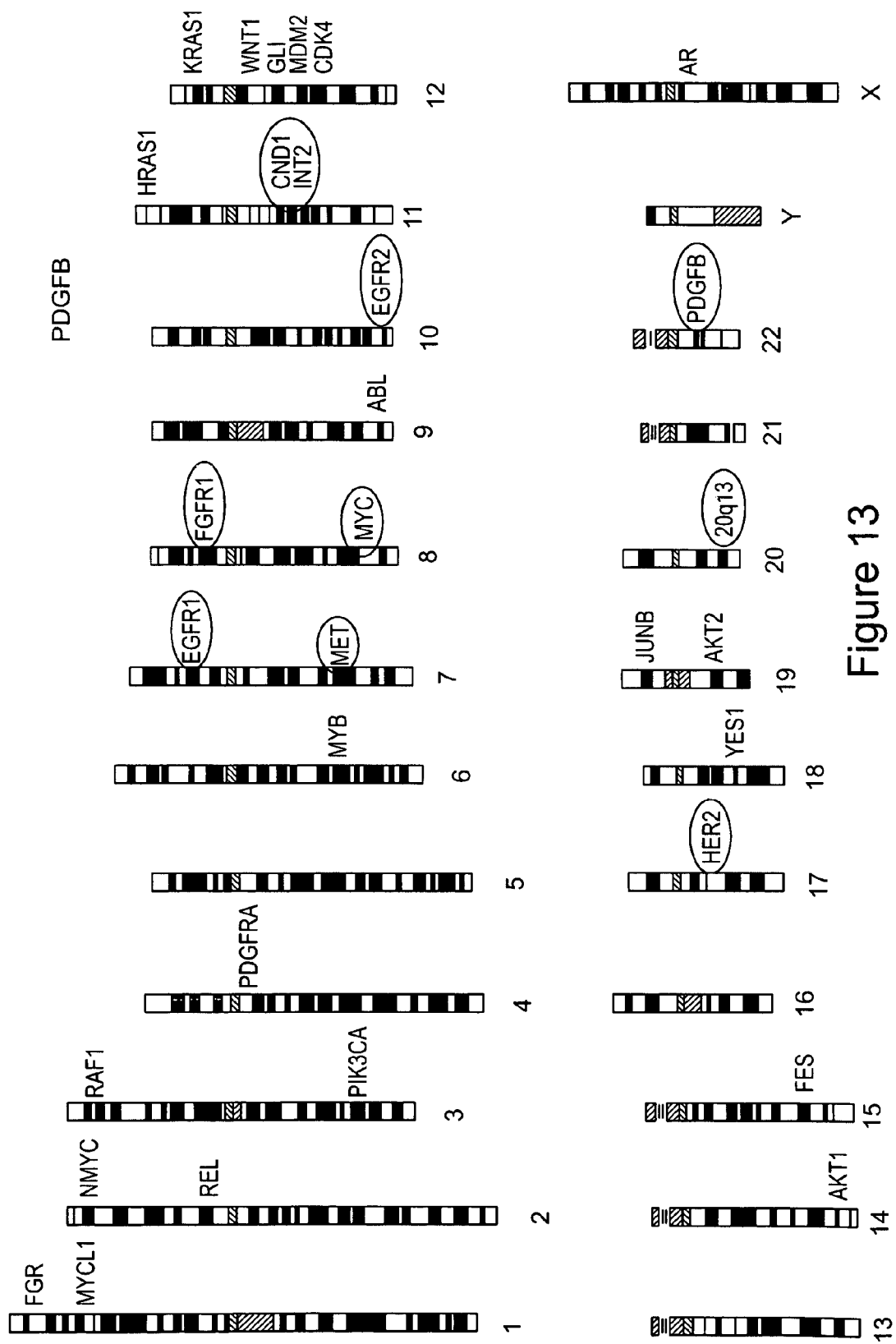
FIG. 13 is a schematic representation of a genosensor CGH microarray that contains 31 target loci that have been reported to undergo amplification in cancer. Circles around target loci indicate amplifications found in the breast cancer cell lines tested in this study.

This system may be used for expression analysis or genomic applications, such as an analysis of genetic changes in cancer. For this purpose a microarray was developed for the specific analysis of all genetic regions that have been reported so far to be associated with tumor formation through amplification at the genome level. The AmpliOnc™ chip contains 33 targets (mostly known oncogenes), each replicated 5 times. A schematic representation of such a chip (and 31 of the targets) is shown in FIG. 13. New chips containing 50 targets or more can also be used.

Example 10

Figure 14:
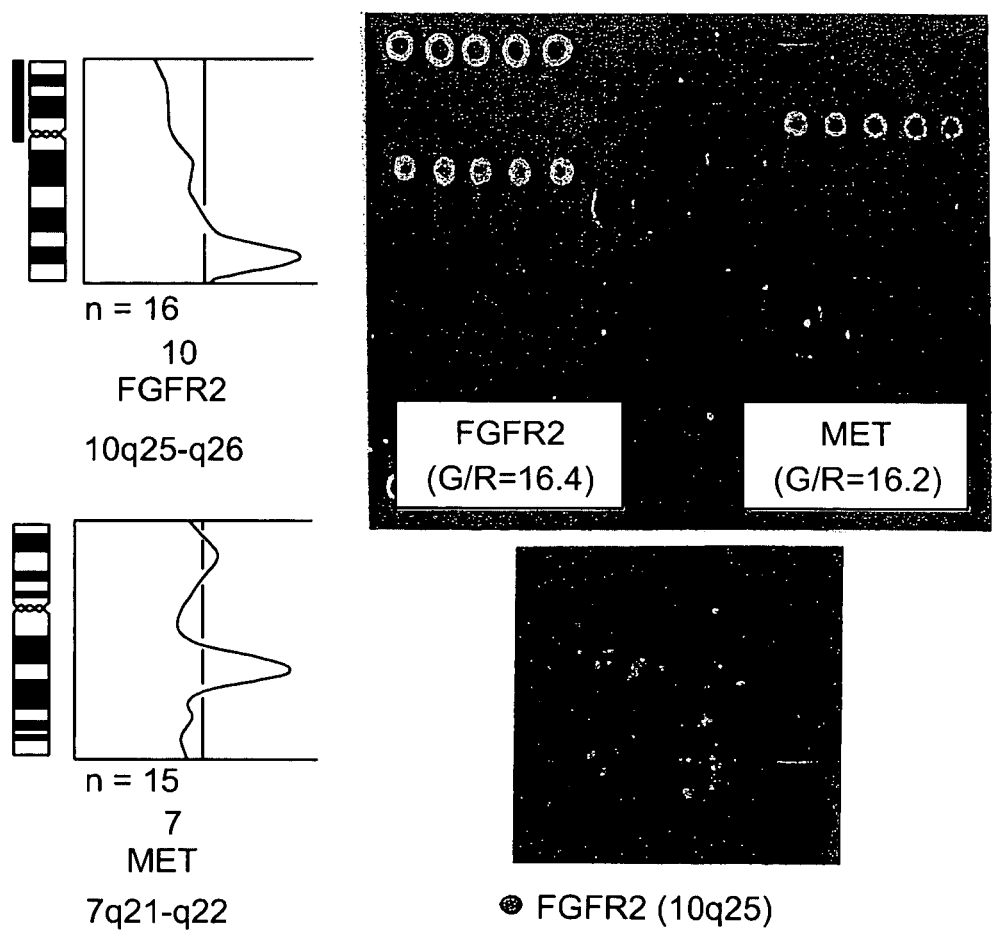
FIG. 14 is a digital representation of the results of a chromosomal CGH analysis showing high level amplifications in Sum-52 breast cancer cells at 10q25-q26 and at 7q21-q22, a genosensor CGH analysis indicating high level amplifications of the MET (7q21) and FGFR2 (10q25) oncogenes, and a FISH analysis showing amplification of FGFR2 (at 10q25).

Combination of Microarrays to Detect Amplification of FGFR2 Gene in Sum-52 Breast Cancer Cell Line This Example demonstrates how target genes for chromosomal gains seen by comparative genomic hybridization (CGH) can be rapidly identified and studied for their clinical relevance using a combination of novel, high-throughput microarray strategies. CGH to metaphase spreads (FIG. 14, chromosomal CGH) showed high-level DNA amplifications at chromosomal regions 7q31, 8p11-p12 and 10q25 in the Sum-52 breast cancer cell line. Genomic DNA from the Sum-52 cell line was then hybridized to a novel CGH microarray (FIG. 14, genosensor CGH, Vysis, Downers Grove, Ill.), which enabled simultaneous screening of copy number at 31 loci containing known or suspected oncogenes (the loci are shown in FIG. 13). This gCGH analysis implicated specific, high-level amplifications of the MET (at 7q31) and FGFR2 (at 10q25) genes, as well as low level amplification of the FGFR1 gene (at 8p11-p12), indicating the involvement of these three genes in the amplicons seen by conventional CGH analysis.

Figure 15:
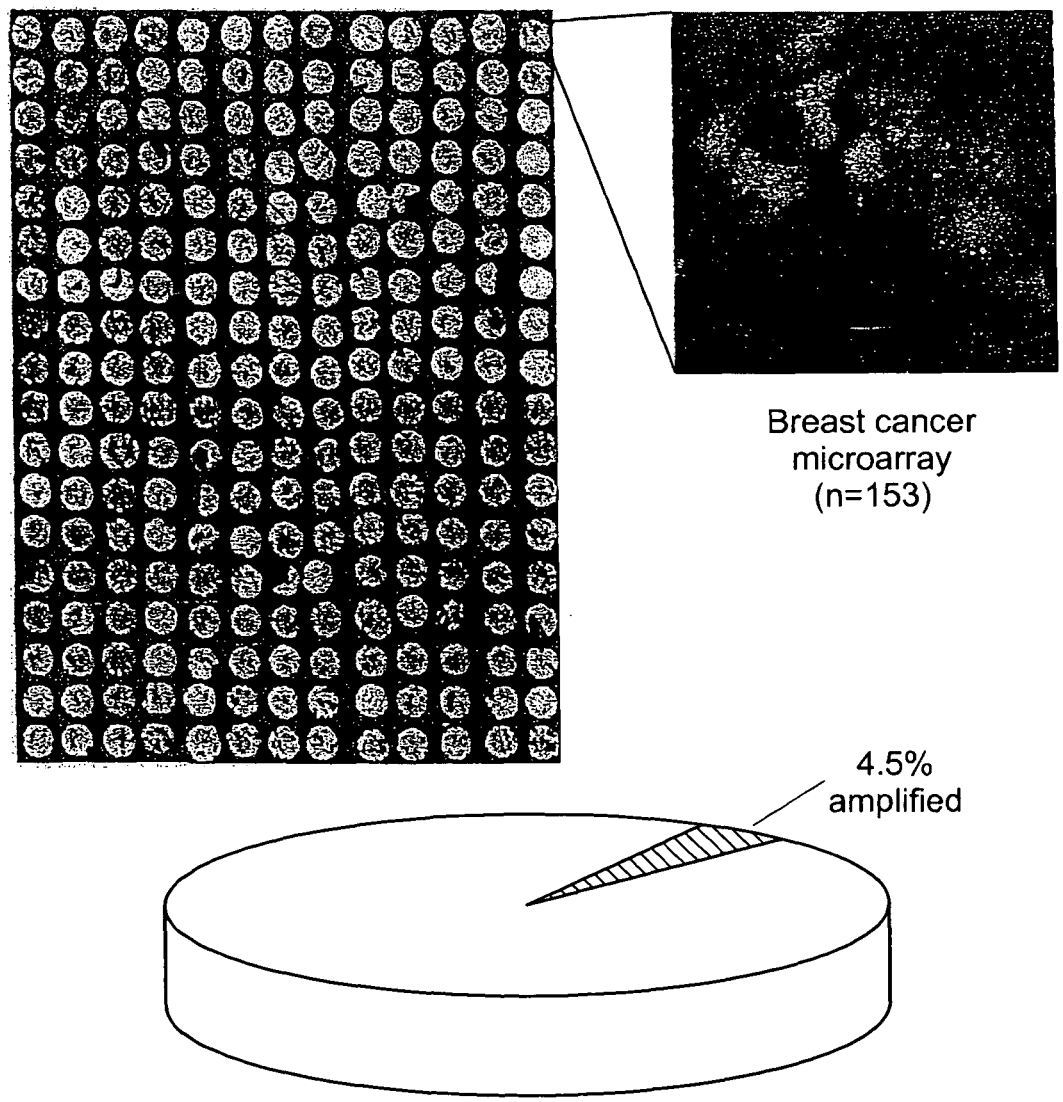
FIG. 15 is a schematic diagram of a breast cancer tissue microarray, as well as a digital image of a hybridization, showing that FGFR2 was amplified in 4.5% of the tumor samples in the breast cancer tissue microarray.

A large-scale expression survey of the same cell line using a cDNA microarray (Clonetech Inc.) provided additional information. The FGFR2 gene was the most abundantly overexpressed transcript in the SUM-52 cells implicating this gene as the likely amplification target gene at 10q25. Overexpression of FGFR2 was confirmed by Northern analysis, and amplification by fluorescence in situ hybridization (FISH). Finally, FISH to a tissue microarray consisting of 145 primary breast cancers (FIG. 15) showed the in vivo amplification of the FGFR2 gene in 4.5% of the cases.

Figure 16:
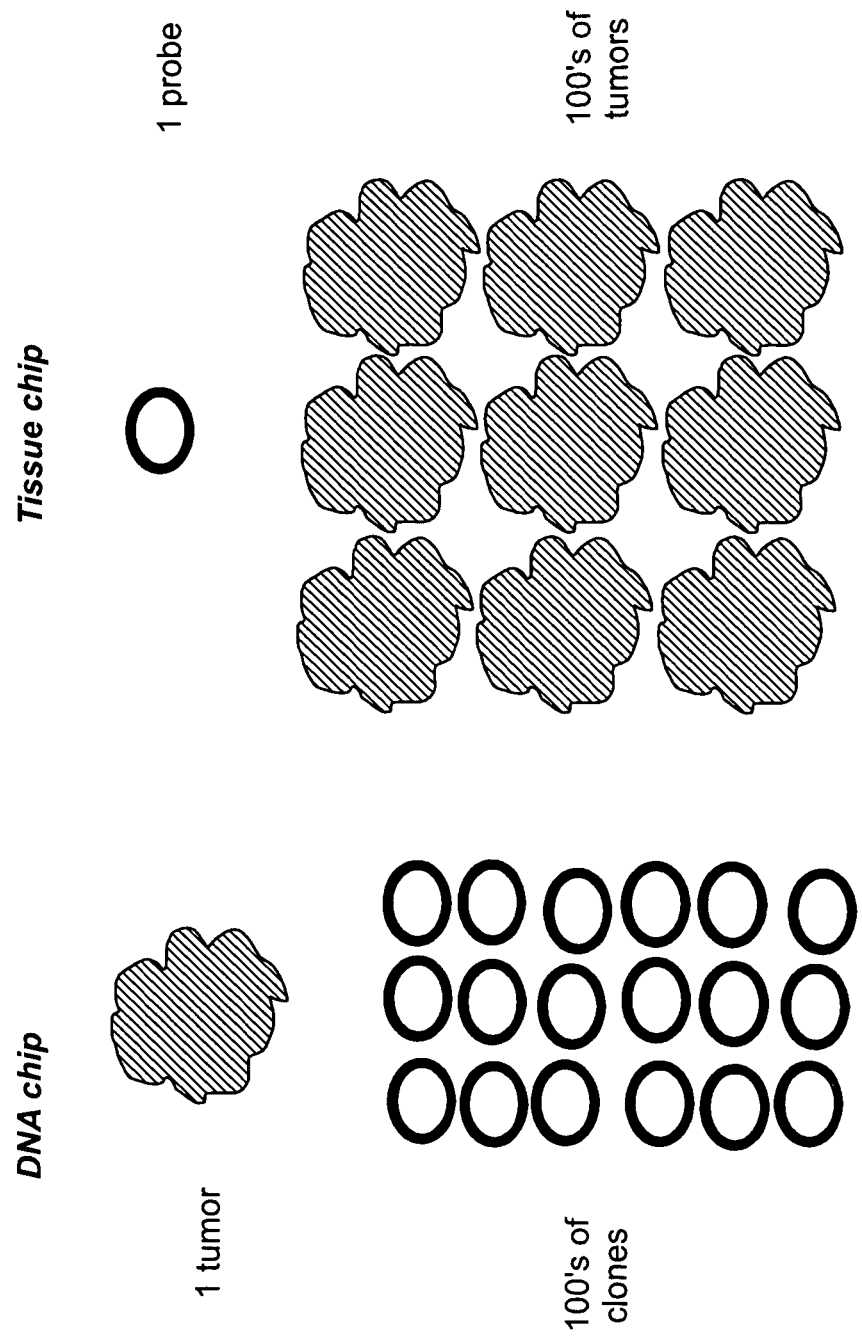
FIG. 16 is a schematic representation of the combination of the DNA array and the tissue array, showing that the DNA array can probe a single tumor with hundreds of probes, while the tissue array technology can conversely probe specimens from hundreds of tumors with a single probe.

These three microarray experiments can be accomplished in a few days, and illustrate how the combination of microarray-based screening techniques is very powerful for the rapid identification of target genes for chromosomal rearrangements, as well as for the evaluation of the prevalence of such alterations in large numbers of primary tumors. This power is conferred by the ability to screen many genes against one tumor, using DNA array technologies (such as cDNA chips or CGH), to find a gene of interest, in combination with the ability to screen many tumors against the gene of interest using the tissue microarray technology. FIG. 16 illustrates that the DNA chip can use multiple clones (for example more than 100 clones) to screen a single tumor or other cell, while the complementary tissue microarray technology can use a single probe to screen multiple (for example more than 100) tumor or other tissue specimens (of either the same or different tissue types).

Example 11

Tissue Arrays to Determine Frequency and Distribution of Gene Expression and Copy Number Chances During Cancer Progression Tissue arrays may be used to follow up genes and targets discovered from, for example, high-throughput genomics, such as DNA sequencing, DNA microarrays, or SAGE (Serial Analysis of Gene Expression) (Velculescu et al., *Science*, 270:484-487, 1995). Comparative analysis of gene expression patterns with cDNA array technology (Schena 1995 and 1996) provides a high-throughput tool for screening expressional changes for better understanding molecular mechanisms responsible for tumor progression as well as aiming for discovery of new prognostic markers and potential therapeutic targets. Tissue arrays provide accurate frequency and distribution information concerning such genes in both pathological and normal physiological conditions.

An example is the use of a prostate tumor array to determine that IGFBP2 (Insulin Growth factor binding protein 2) is a marker associated with progression of human prostate cancer. To elucidate mechanisms underlying the development and progression of hormone refractory prostate cancer, gene expression profiles were compared for four independent CWR22R hormone refractory xenografts to androgen dependent CWR22 primary xenograft. The CWR22 xenograft model of human prostate cancer was established by transplantation of human prostate tumor cells into the nude mouse (Pretlow, *J. Natl. Cancer Inst.*, 3:394-398, 1993). This parental tumor xenograft is characterized by secretion of prostate specific antigen (PSA) and with rapid reduction of tumor size in response to the hormone-withdrawal therapy. Approximately half of the treated animals will develop recurrent tumors from a few weeks to several months. These recurrent tumors are resistant to further hormonal treatments when transferred to the new host. They also are characterized by a more aggressive phenotype than parental CWR22 tumors, and eventually lead to death of the animal. This experimental model mimics the course of prostate cancer progression in human patients.

Comparison of the expression levels of 588 known genes during the progression of the CWR22 prostate cancer in mice was performed with the cDNA microarray technology. RNA was prepared from CWR22 xenografts as described earlier with minor modifications (Chirgwin, 1979). The mRNA was purified using oligo(dT) selection with DynaBeads (Dynal) according to manufacturers instructions. The cDNA array hybridizations were performed on AtlasII cDNA arrays (Clontech) according to manufacturers instructions. The cDNA probes were synthesized using 2 µg of polyA$^+$ RNA and labeled with 32P a dCTP.

The gene expression pattern in a hormone-sensitive CWR22 xenograft was compared with that of a hormone-refractory CWR22R xenograft. Expressional changes of several genes, which have previously been shown to be involved in prostate cancer pathogenesis were detected. In addition multiple genes were identified with no previous connection to prostate cancer, nor had they been known to be regulated by androgens. One of the most consistently upregulated genes, Insulin-like Growth Factor Binding Protein 2 (IGFBP-2), was chosen for further study. The tissue microarray technology was used to validate that the IGFBP2 expression changes also take place in vivo, during the progression of prostate cancer in patients undergoing hormonal therapy.

Formalin-fixed and paraffin-embedded samples from a total of 142 prostate cancers were used for construction of the prostate cancer tissue microarray. The tumors included 188 non-hormone refractory primary prostate cancers, 54 transurethral resection specimens of locally recurrent hormone-refractory cancers operated during 1976-1997, and 27 transurethral resections for BPH as benign controls. The subset of the primary non-hormone refractory tumors and benign controls was selected from the archives of the Institute for Pathology, University of Basel, (Switzerland), and the subset of hormone-refractory tumors from the University of Tampere (Finland). The group of primary non-hormone refractory prostate cancers consisted of 50 incidentally detected tumors in transurethral resections for presumed BPH (pT1a/b), and 138 radical prostatectomy specimens of patients with clinically localized disease. The specimens were fixed in 4 percent phosphate-buffered formalin. The sections were processed into paraffin and slides were cut at 5 µm and stained with haematoxylin and eosin (H & E). All sections were reviewed by one pathologist, and the most representative (usually the least differentiated) tumor area was delineated on the slide. The tissue microarray technology was used as previously described to construct the tissue array.

Standard indirect immunoperoxidase procedures were used for immunohistochemistry (ABC-Elite, Vector Laboratories). The goat polyclonal antibody IGFBP-2, C-18 (1:x, Santa Cruz Biotechnology, Inc., California) was used to detect IGFBP-2 after a microwave pretreatment. The reaction was visualized by diaminobenzidine as a chromogen. Positive controls for IGFBP-2 consisted of normal renal cortex. The primary antibody was omitted for negative controls. The intensity of the cytoplasmic IGFBP-2 staining was estimated and stratified into 4 groups (negative, weak, intermediate, and strong staining).

There was a strong relationship between IGFBP-2 staining and progression of cancer to a hormone refractory disease with an increasing frequency of high-level staining. Strong IGFBP-2 staining was present in none of the normal glands, in 30% of the non-hormone-refractory primary tumors but in 96% of the recurrent, hormone-refractory prostate cancers (p=0.0001). Hence, this example provides another case in which a high-throughput expression survey by cDNA array hybridization indicated a specific gene, which may be involved in disease progression. This hypothesis could be directly validated using the tissue array technology. The results have identified IGFBP2 to be used as a target for developing diagnostic, prognostic or therapeutic approaches to the management of patients with advanced prostate cancer.

Example 12

PDGFB in Breast Cancer

The breast cancer SKBR3 cell line was screened with the AmpliOnc™ DNA array, and Platelet Derived Growth Factor B (PDGFB) was identified as being amplified. Using this information, a PDGFB probe was made using a clone identical to the PDGFB clone used in the AmpliOnc™ array. This probe was used to screen a breast cancer tumor array. It was found that only 2% of all the breast cancers screened were amplified for PDGFB. A multi-tumor array (described in Example 6) was then probed using this probe. This revealed that, unexpectedly, the PDGFB gene was amplified in a large percentage of lung and bladder cancers. Thus, using the invention, a novel marker of diagnostic importance in these other types of tumors was identified.

Example 13

Herceptin Treatment

Tissue arrays can be used to screen large numbers of tumor tissue samples to determine which tumors would be susceptible to a particular treatment. For example, a breast cancer array can be screened for expression of the HER-2 gene (also called ERBB2 in Example 1), as explained in Example 1. Tumors that over-express and/or amplify the HER-2 gene may be good candidates for treatment with herceptin, which is an antibody that inhibits the expression of HER-2. Screening of the multi-tumor tissue array with the HER-2 antibodies or a DNA probe would provide information about cancers other than breast cancer that could be successfully treated with the Herceptin therapy.

Example 14

Correlating Prognosis and Survival with Markers

Tumor tissue arrays constructed from tumors taken from patients for whom history and outcome is known may be used to assess markers with prognostic relevance. This example illustrates that prognostic markers in urinary bladder cancer can be evaluated using tumor tissue arrays, in spite of any intratumor heterogeneity.

An array of 315 bladder tumors was analyzed for nuclear p53 accumulation by immunohistochemistry. The p53 analysis was done twice; once on conventional large histological sections taken from entire tumor blocks and once on a section from a tumor array containing one sample from each tumor.

The tumor series consisted of 127 pTa, 81 pT1, and 128 pT2-4 bladder carcinomas with clinical follow up information (tumor specific survival).

One block per tumor was analyzed. One section was taken from each block for immunohistochemical analysis. Then a tissue array was constructed by taking one "punch biopsy" from each block and bringing it in an empty recipient block. Sections 4 μm thick were taken from primary tumor blocks and from the array block. The monoclonal antibody DO-7 (DAKO, 1:1000) was applied for immunostaining using standard procedures.

On large sections, a tumor was considered positive if moderate or strong nuclear p53 staining was seen in at least 20% of tumor cells, at least in an area of the tumor. On array sections, a tumor was considered positive if moderate or strong nuclear p53 staining was seen in at least 20% of arrayed tumor cells. Weak nuclear and any cytoplasmic p53 staining was disregarded.

A Chi-square test was used to compare the p53 results between array and large sections. Survival curves were plotted according to Kaplan-Meier. A log rank test was applied to examine the relationship between p53 positivity and tumor specific survival. Surviving patients were censored at the time of their last clinical control. Patients dying from causes other than their bladder tumor were censored at the time of death.

Results showed that p53 could be analyzed on 315 arrayed tumor samples (21 samples were absent on the p53 stained array section). On conventional sections, p53 immunostaining was positive in 105 of these 315 tumors which were also present on the array. p53 positivity as detected on conventional "large" sections was significantly linked to poor prognosis (FIG. 1A, p<0.0001). Only 69 of these 105 tumors (66%) that were p53 positive on large sections were also positive on arrayed tumor samples, while 36 (34%) remained negative probably because of tumor heterogeneity. Nevertheless, there was a strong association between p53 immunostaining results on arrays and on large sections (p<0.0001) and p53 positivity on arrays was still significantly linked to poor prognosis (FIG. 1B, p=0.0064).

The specific number of biopsies from each tumor that are preferably obtained to reproduce 90%, 95%, or 100% of the information obtained from the whole-section analysis will make it possible to determine how many "punches" with the tissue arrays are required to extract clinically significant information from the tissue array experiments. This optimal number may vary depending on the tumor type and the specific biological target that will be analyzed.

Example 15

Novel Gene Targets

Tissue arrays may be used to find novel targets for cancer and other therapies. Hundreds of different genes may be differentially regulated in a given cancer (based on cDNA, e.g., microarray, hybridizations, or other high-throughput expression screening methods such as sequencing or SAGE). Analysis of each gene candidate on a large tissue array can help determine which is the most promising target for development of novel drugs, inhibitors, etc. For instance, a tumor array containing thousands of diverse tumor samples may be screened with a probe for an oncogene, or a gene coding for a novel signal transduction molecule. Such a probe can bind to one or a number of different tumor types. If a probe reveals that a particular gene is overexpressed and/or amplified in many tumors, then that gene may be an important target, playing a key role in many tumors of one histological type or in different tumor types. Therapies directed to interfere with the expression of that gene, or with the function of the gene product of that gene, may be promising novel cancer drugs. In particular, the tissue arrays can be used to help prioritize the selection of targets for drug development.

Example 16

Tissue Array Followed by DNA Array

Although many of the foregoing examples have described the DNA array being used prior to the tissue array, the present invention includes use of these arrays in either order, or in combination with other analytic techniques. Hence, genes of interest noted when probing multiple tumor samples with a single probe during tissue array analysis can subsequently be selected to be placed on a DNA array, using a unique sequence from the gene of interest as one of the probes attached to the array substrate. For example, one could tailor a DNA chip that has most diagnostic, prognostic, or therapeutic relevance based on information from the microarray experiment.

Figure 17:
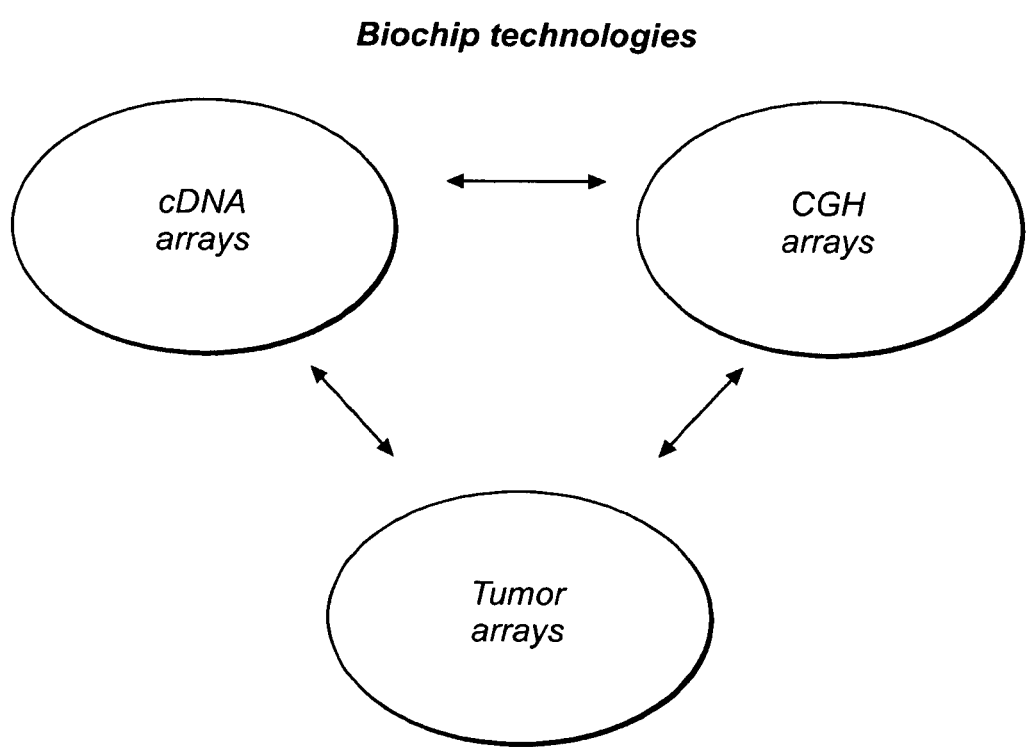
FIG. 17 is a schematic diagram representing the combination of the tissue array technology with cDNA and/or CGH arrays.

Some possible interrelationship of cDNA arrays, CGH arrays, and tissue arrays is shown in FIG. 17. As illustrated in that figure, the various assays can be performed in any order, or in any combination.

Example 17

Cell Line Arrays

Cultured cells or cells isolated from non-solid tissues or tumors (such as blood samples, bone marrow biopsies, or cytological specimens obtained by needle aspiration biopsies) can also be analyzed with the tissue array techniques. This is an important extension of the tissue array technology to the analysis of individual cells, or populations of cells, obtained either directly from people or animals or after various incubations of cell culture experiments have been performed in vitro (such as a specific hormonal or chemotherapeutic test performed on a microtiter tray format for pharmaceutical drug screening) In the analysis of malignancies, this would enable analysis of leukemias and lymphoma tissues or other liquid tumor types following the same strategies described above for solid tumors.

Using this approach, cancer cell lines obtained from the American Type Culture Collection (Rockville, Md.) were used. Cells were trypsinized and the cell suspensions were spun down with a centrifuge at 1200×g. The cell pellet was fixed with alcohol-based and formaldehyde fixatives, and the fixed cell pellet was embedded in paraffin following routine protocols used in pathology laboratories. The fixed and embedded cell suspensions can then be used as starting material for the development of cell arrays, using the same procedure as described previously for the fixed and embedded tissue specimens. It is anticipated that up to or at least 1000 different cell populations can be arrayed in a single standard-size paraffin block using this method.

Very small punch sizes (for example less than 0.5 mm) can be used for creating arrays from homogenous cultured cells. This allows high density arrays to be constructed. For example, approximately 2000 different cell populations can be placed in a single 40 mm×25 mm paraffin block.

The methods of analyzing tissue in accordance with the present invention can take many different forms, other than those specifically disclosed in the above examples. The tissue specimens need not be abnormal, but can be normal tissue analyzed for function and tissue distribution of a specific gene, protein, or other biomarker (where a biomarker is a biological characteristic that is informative about a biological property of the specimen). The normal tissue could include embryonal tissues, or tissues from a genetically modified organism, such as a transgenic mouse.

The array technologies can also be used to analyze diseases that do not have a genetic basis. For example, the gene or protein expression patterns that are likely to have importance for the pathogenesis or diagnosis of a disease can be profiled. The tissue specimens need not be limited to solid tumors, but can also be taken from cell lines, hematological or other liquid tumors, cytological specimens, or isolated cells.

Cells of humans or other animals can be used in a suspension, as may cells of yeast or bacteria. Alternatively, cells in suspension can be spun down in a centrifuge to provide a solid or semi-solid pellet, fixed, and then placed in the array, much like a tissue specimen. Liquid cellular suspensions can be placed with a pipette into a matrix (for example depressions in a slide surface) and then can be analyzed in the same manner as the tissue array already described. The tissue arrays can also be used in cell line experiments, such as high throughput chemotherapeutic screening of cells grown on microtiter plates. The cells from each well are treated with a different drug or a different concentration of the drug, and are then recovered and inserted into a cell line microarray to analyze their functional characteristics, morphology, viability and expression of specific genes brought about by the drug treatment.

Histological or immunological analyses that can be used with the array include, without limitation, a nucleic acid hybridization, PCR (such as in situ PCR), PRINS, ligase chain reaction, pad lock probe detection, histochemical in situ enzymatic detection, and the use of molecular beacons. The tissue array technology can be used to directly collect specimens (tissues or cells) from humans, animals, cell lines, or other experimental systems. For example, when biopsy specimens are treated in a conventional manner in pathology laboratories, after fixation, the specimens are routinely inserted horizontally in a paraffin block. Therefore, it is very difficult, if not impossible to acquire specimens from such tissues into a tissue array. However, if multiple biopsy specimens obtained from surgery are directly fixed (and, if required, embedded in a suitable medium, such as paraffin) and then inserted directly vertically into a matrix, this would enable construction of a tissue array of biopsy specimens. Such an array would be useful for research purposes or in a clinical setting to e.g. monitor progression of premalignant lesions or monitor treatment responses (with molecular markers) from metastatic tumors that cannot be surgically removed.

Cytological specimens (such as fine needle aspirations, cervical cytology, blood specimens, isolated blood cells, or urine cells) can be pelleted by centrifugation and then fixed and embedded for arraying as explained previously. Alternatively, cells can be fixed in a suspension, and directly inserted (e.g., pipetted) into holes in a matrix or embedded first, and then arrayed. This will provide an array of cells for research or for, diagnostic purposes. This would enable rapid cytological diagnostics where multiple specimens from different patients can be screened simultaneously from a single slide, not only for their morphology, but for their molecular characteristics. This would also enable automation of the analysis, since a number of specimens can be screened with a microscope, automated image analysis system, scanner or associated expert systems at once. The use of such cellular preparations is particularly important for the diagnosis of hematological disorders, such as leukemias and lymphomas. This would also allow automation of lymphocyte typing from many patients at once, whose specimens are inserted in an array format for immunophenotyping or for analysis by in situ hybridization. Screening of donated blood specimens for viral antigens, viral DNA, or other pathogens in a blood bank could similarly be performed in an array format.

Arrays of tumor progression can also be constructed by collecting specimens from a subject at different stages of progression of the subject's tumor (such as progression to hormone refractory prostate cancer). Alternatively, tumors of different stages from different subjects can be collected and incorporated into the array. The array can also be used to follow the progression of pre-neoplastic lesions (such as the evolution of cervical neoplasia), and the effects of chemoprevention agents (such as the effects of anti-estrogens on breast epithelium and breast cancer development).

In another embodiment, specimens from a transgenic or model organism can be obtained at different stages of development of the organism, such as different embryonic stages, or different ages after birth. This enables the study of things such as normal and abnormal embryonic development.

The biological analyses that are performed on the microarray sections can be any analysis performed on regular tissue sections. Arrays can also be assembled from one or more tumors at different stages of progression, such as normal tissue, hyperplasia, in situ cancer, invasive cancer, recurrent tumor, local lymph node metastases, or distant metastases.

An "EST" or "Expressed Sequence Tag" refers to a partial DNA or cDNA sequence, typically of between 50 and 500 sequential nucleotides, obtained from a genomic of cDNA library, prepared from a selected cell, cell type, tissue or tissue type, organ or organism, which corresponds to an mRNA of a gene found in that library. An EST is generally a DNA molecule.

"Specific hybridization" refers to the binding, duplexing, or hybridizing of a molecule only to a Particular nucleotide sequence under stringent conditions when that sequence is present in a complex mixture (e.g., total cellular) DNA or RNA.

Other Embodiments

In view of the many possible embodiments to which the principles of the invention can be applied, it should be recognized that the illustrated embodiments are examples of the invention, and should not be taken as a limitation on the scope of the invention. Rather, the scope of the invention is defined by the following claims. We therefore claim as our invention all that comes within the scope and spirit of these claims.

The invention claimed is:

1. A method of detecting the presence of cancerous cells in a human breast tissue specimen, the method comprising:
   a) obtaining a breast tissue specimen,
   b) providing a probe set consisting of two or more labeled probes selected from a locus specific probe for chromosomal region 7q31, a locus specific probe for chromosomal region 8p11-p12, a locus specific probe for chromosomal region 10q25 and a probe specific for PDGFB, wherein at least one probe is specific for PDGFB,
   c) contacting said specimen with said two or more labeled probes of b), and
   d) detecting the presence of cancerous cells when PDGFB and at least one of the chromosomal regions of step b) are amplified in the human breast tissue specimen.

2. The method of claim 1, wherein said 10q25 amplification is detected by polymerase chain reaction (PCR).

3. The method of claim 1, wherein said 10q25 amplification is detected by fluorescence in situ hybridization (FISH).

4. The method of claim 1, wherein polymerase chain reaction (PCR) is used to determine if amplification is present.

5. The method of claim 1, wherein fluorescence in situ hybridization (FISH) is used to determine if amplification is present.

6. The method of claim 1, wherein a cDNA microarray is used to determine if amplification is present.

* * * * *